US010053455B2

(12) United States Patent
Benjahad et al.

(10) Patent No.: US 10,053,455 B2
(45) Date of Patent: Aug. 21, 2018

(54) DIAZASPIROALKANEONE-SUBSTITUTED OXAZOLE DERIVATIVES AS SPLEEN TYROSINE KINASE INHIBITORS

(71) Applicant: AB SCIENCE, Paris (FR)

(72) Inventors: Abdellah Benjahad, Champigny sur Marne (FR); Jason Martin, L'hay-les-roses (FR); Claire Schalon, Gif-sur-yvette (FR); Didier Pez, Nievroz (FR); Emmanuel Chevenier, Les Ulis (FR); Franck Sandrinelli, Balan (FR); Willy Picoul, Lyons (FR); Alain Moussy, Paris (FR)

(73) Assignee: AB SCIENCE, Paris (FR)

( * ) Notice: Subject to any disclaimer, the term of this patent is extended or adjusted under 35 U.S.C. 154(b) by 179 days.

(21) Appl. No.: 15/128,743

(22) PCT Filed: Mar. 23, 2015

(86) PCT No.: PCT/EP2015/056047
§ 371 (c)(1),
(2) Date: Sep. 23, 2016

(87) PCT Pub. No.: WO2015/144614
PCT Pub. Date: Oct. 1, 2015

(65) Prior Publication Data
US 2018/0179195 A1 Jun. 28, 2018

Related U.S. Application Data

(60) Provisional application No. 61/969,479, filed on Mar. 24, 2014.

(51) Int. Cl.
*C07D 413/14* (2006.01)
*C07D 417/14* (2006.01)
*A61K 31/5377* (2006.01)
*A61K 31/506* (2006.01)

(52) U.S. Cl.
CPC .......... *C07D 413/14* (2013.01); *A61K 31/506* (2013.01); *A61K 31/5377* (2013.01); *C07D 417/14* (2013.01)

(58) Field of Classification Search
CPC .. C07D 413/14; C07D 417/14; A61K 31/506; A61K 31/5377
See application file for complete search history.

(56) References Cited

U.S. PATENT DOCUMENTS

| 3,740,420 A | 6/1973 | Herschler et al. |
| 3,743,727 A | 7/1973 | Herschler |
| 3,989,816 A | 11/1976 | Rajadhyaksha |
| 4,322,433 A | 3/1982 | Leslie et al. |
| 4,379,454 A | 4/1983 | Campbell et al. |
| 4,405,616 A | 9/1983 | Rajadhyaksha |
| 4,411,893 A | 10/1983 | Johnson et al. |
| 4,460,372 A | 7/1984 | Campbell et al. |
| 4,575,515 A | 3/1986 | Sandborn |
| 4,615,699 A | 10/1986 | Gale et al. |
| 5,556,611 A | 9/1996 | Biesalski |
| 5,906,202 A | 5/1999 | Schuster et al. |
| 2006/0199804 A1 | 9/2006 | Hummersone et al. |
| 2013/0035331 A1* | 2/2013 | Moussy ............... C07D 413/12 514/227.8 |

FOREIGN PATENT DOCUMENTS

| WO | 2005075468 | 8/2005 |
| WO | 2011086085 | 7/2011 |
| WO | 2013192098 | 12/2013 |

OTHER PUBLICATIONS

International Search Report issued in International Application No. PCT/EP2015/056047 dated May 6, 2015 (4 pages).
Written Opinion issued in International Application No. PCT/EP2015/056047 dated May 6, 2015 (7 pages).
Diaz-Granados et al.: "Dextran Sulfate Sodium-Induced Colonic Histopathology, but not Altered Epithelial Ion Transport, Is Reduced by Inhibition of Phosphodiesterase Activity"; American Journal of Pathology, Jun. 2000, vol. 156, pp. 2169-2177.
Humbert et al.: "Masitinib, a c-kit/PDGF receptor tyrosine kinase inhibitor, improves disease control in severe corticosteroid-dependent asthmatics"; Allergy, 2009, vol. 64, pp. 1194-1201.
Tebib et al.: "Masitinib in the treatment of active rheumatoid arthritis: results of a multicentre, open-label, dose-ranging, phase 2a study"; Arthritis Research & Therapy, 2009, vol. 11, No. 3, pp. 1-12.
Benjahad et al.: "Synthesis and Antiretroviral Evaluation of 3-Alkyd 2-Piperazinone Nucleoside Analogs"; Tetrahedron Letters, 1994, vol. 35, No. 51, pp. 9545-9548.
Cooper et al.: "Interaction of Surfactants with Epidermal Tissues: Physicochemical Aspects"; Surfactant Interaction with Epidermis, pp. 195-211.
McAdoo et al.: "Fostamatinib Disodium"; Drugs Future, vol. 36, pp. 1-10.
Dugard et al.: "Effects of Ionic Surfactants on the permeability of Human Epidermis: an Electrometric Study"; The Journal of Investigative Dermatology, 1973, vol. 60, No. 5, pp. 263-269.
Iwaki et al.: "Development of hypoxia-sensitive Gd3+-based MRI contrast agents"; Bioorganic & Medical Chemistry Letters, 2012, vol. 22, pp. 2798-2802.
Maligres et al.: "Nosylaziridines: Activated Aziridine Electrophiles"; Tetrahedron Letters, 1997, vol. 38, No. 30, pp. 5253-5256.
Okamura et al.: "Identification of Seven Genes Regulated by Wild-Type p53 in a Colon Cancer Cell Line Carrying a Well-Controlled Wild-Type p53 Expression System"; Oncology Research, 1999, vol. 11, pp. 281-285.

(Continued)

*Primary Examiner* — Timothy R Rozof
(74) *Attorney, Agent, or Firm* — Hamre, Schumann, Mueller & Larson, P.C.

(57) ABSTRACT

The present invention is concerned with substituted oxazole derivatives that selectively modulate, regulate, and/or inhibit signal transduction mediated by certain native and/or mutant protein kinases implicated in a variety of human and animal diseases such as cell proliferative, metabolic, autoimmune, allergic, and degenerative disorders. In particular, the presently disclosed compounds are Syk inhibitors.

19 Claims, No Drawings

(56) References Cited

OTHER PUBLICATIONS

Remington's Pharmaceutical Sciences, Mack Publishing Company, 16th Edition, Pennsylvania, 1980, pp. 1-28.
Sekura et al: "The Percutaneous Absorption of Alkyl Methyl Sulfoxides"; The Proctor and Gamble Company, 1972, pp. 257-269.
Takada et al: "TNF Activates Syk Protein Tyrosine Kinase Leading to TNF-Induced MARK Activation, NF-B Activation, and Apoptosis"; The Journal of Immunology, 2004, pp. 1064-1077.
Van Leusen et al.: "A Novel and Efficient Synthesis of Oxazoles from Tosylmethylisocyanide and Carbonyl Compounds"; Department of Organic Chemistry, 1972, pp. 2369-2372.
Wong et al.: "Targeting Syk as a treatment for allergic and autoimmune disorders"; Expert Opinion Investigation Drugs, 2004, vol. 13, pp. 743-762.
Yamada et al.: "IL-1 Induced Chemokine Production Through the Association of Syk with TNF Receptor-Associated Factor-6 in Nasal Fibroblast Lines!"; The Journal of Immunology, 2001, pp. 282-288.

\* cited by examiner

DIAZASPIROALKANEONE-SUBSTITUTED OXAZOLE DERIVATIVES AS SPLEEN TYROSINE KINASE INHIBITORS

The present disclosure discloses substituted oxazole derivatives that selectively modulate, regulate, and/or inhibit signal transduction mediated by certain native and/or mutant protein kinases implicated in a variety of human and animal diseases such as cell proliferative, metabolic, autoimmune, allergic, and degenerative disorders. In particular, several of these compounds are potent and selective spleen tyrosine kinase (Syk) inhibitors.

BACKGROUND

Protein Kinases are receptor type or non-receptor type proteins, which transfer the terminal phosphate of ATP to aminoacid residues, such as tyrosine, threonine, serine residues, of proteins, thereby activating or inactivating signal transduction pathways. These proteins are known to be involved in many cellular mechanisms, which in case of disruption, lead to disorders such as abnormal cell proliferation and migration as well as inflammation.

As of today, there are over 500 known Protein kinases. Included are the well-known Abl, Akt1, Akt2, Akt3, ALK, Alk5, A-Raf, Axl, B-Raf, Brk, Btk, Cdk2, Cdk4, Cdk5, Cdk6, CHK1, c-Raf-1, Csk, EGFR, EphA1, EphA2, EphB2, EphB4, Erk2, Fak, Fes, Fer, FGFR1, FGFR2, FGFR3, FGFR4, Flt-3, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mer, MNK1, MLK1, mTOR, p38, PDGFRα, PDGFRβ, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, RON, Src, Stk6, Syk, TEC, Tie2, TrkA, TrkB, Tyk2, VEGFR1/Flt-1, VEGFR2/Kdr, VEGFR3/Flt-4, Yes, and Zap70.

Spleen tyrosine kinase (Syk), an intracellular protein tyrosine kinase, is a key mediator of immunoreceptor signalling in a host of inflammatory cells including B cells, mast cells, macrophages, and neutrophils (Wong Br et al (2004), *Expert Opin. Investig. Drugs*, 13, 743-762). Syk is also widely expressed in nonhematopoietic cells like fibroblasts, breast cancer cells, colonic carcinoma cells, hepatocytes, neuronal cells, and vascular endothelial cells (Okamura S et al (1999), *Onco. Res.* 11, 281-285). Originally, Syk was thought to function primarily in signaling of immunoreceptors such as Fc receptor (FcR) and B cell receptor (BCR). However, recent studies demonstrated the crucial role of Syk in the cell signaling of diverse cellular stimuli including IL-1, tumor necrosis factor-α (TNFα), lipopolysaccharide, and β1-integrin (Yamada T et al (2001), *J. Immunol.*, 167, 283-288). For instance, Syk can be activated by TNFα, resulting in MAPK phosphorylation and NF-κB translocation in hematopoietic cell lines (Takada Y and Aggarwal BB (2004), *J. Immunol.*, 173, 1066-1077). IL-1-induced chemokine production in fibroblasts of nasal polyps is also mediated by Syk activation (Yamada T et al (2001), *J. Immunol.*, 167, 283-288). Syk has emerged as a potential therapeutic target for treatment of allergic and autoimmune disorders.

DETAILED DESCRIPTION

Existing compounds active on protein kinases are not always endowed with satisfactory properties such as potency and selectivity. Additionally, existing compounds active on protein kinases are not always endowed with satisfactory in vivo bioavailability. The present disclosure discloses compounds that display potent and selective inhibitory activity on wild type and/or mutated protein kinase, in particular wild type and/or mutated tyrosine kinase, and more particularly Syk. In particular, the present disclosure discloses a method and compounds for selectively modulating, regulating, and/or inhibiting signal transduction mediated by certain native and/or mutant protein kinase, and in particular tyrosine kinases implicated in a variety of human and animal diseases such as cell proliferative, metabolic, autoimmune, allergic, and degenerative disorders. More particularly, these compounds are potent and selective Syk inhibitors. More in particular, the inventors have discovered that compounds displaying specific substitutions in oxazole derivatives are potent and selective inhibitors of Syk tyrosine kinase.

In a first aspect, the present disclosure relates to compounds of formula (I), which may represent either free base forms of the substances or pharmaceutically acceptable salts thereof:

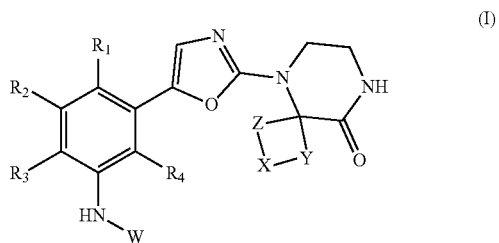

(I)

Wherein:
R1, R2, R3 and R4 are each independently selected from:
hydrogen,
cyano,
$CF_3$,
halogen (selected from F, Cl, Br or I),
an alkyl group optionally substituted with an heterocycle,
an alkoxy group optionally substituted with an heterocycle,
a solubilising group,
a heterocycle,
—CO—NRR',
—$SO_2$—NRR',
—NRR',
—NR—CO—R' and
—NR—$SO_2$R' group
wherein R and R' are each independently hydrogen or alkyl group;
W is aryl or heteroaryl group, unsubstituted or substituted by one or more (for example from one to four, such as one or two or three, for example one) substituents selected from:
cyano,
$CF_3$,
halogen (selected from F, Cl, Br or I),
an alkyl group optionally substituted with an heterocycle,
a cycloalkyl group,
an alkoxy group optionally substituted with an heterocycle,
an aryl group,
a heteroaryl group,
a heterocycloalkyl group,
a solubilising group,
—CO—NRR',
—$SO_2$—NRR',

—NRR',

—NR—CO—R' and

—NR—SO$_2$R' group wherein R and R' are each independently hydrogen or alkyl group;

X is selected from O, S, N(R5), N[C(=O)R6] and (CH$_2$)n wherein n is 0, 1 or 2, R5 and R6 are each independently H or C1-4alkyl group;

Y is (CH$_2$)m wherein m is 1, 2, 3 or 4;

Z is (CH$_2$)p wherein p is 1 or 2.

The present disclosure discloses compounds wherein X may be (CH$_2$)n, n may be 0, 1 or 2 and m and p may be 1. For example, n is 0 and m and p are 1 (thereby obtaining a cyclopropyl). Alternatively, n is 1 and m and p are 1 (thereby obtaining a cyclobutyl). Alternatively, n is 2 and m and p are 1 (thereby obtaining a cyclopentyl).

The present disclosure discloses compounds wherein W may be a substituted, such as monosubstituted, heteroaryl or a substituted, such as monosubstituted, aryl. For example, W is as monosubstituted heteroaryl.

When W is a heteroaryl, the heteroaryl may be a 5-8 membered monocyclic ring. That ring may contain at least one, such as from one to three, for example one or two nitrogen atoms. For example, the heteroaryl is pyrimidine such as pyrimidin-2-yl. An example of W is 4-substituted pyrimidin-2-yl.

The present disclosure discloses compounds wherein each of the substituents of W may be independently selected from the group consisting of cyano, CF$_3$, halogen, an alkyl group optionally substituted with a heterocycle (such as an unsubstituted C1-C3 alkyl, for example methyl, ethyl, propyl), a cycloalkyl group, an alkoxy group optionally substituted with an heterocycle, an aryl group (for example phenyl), an heteroaryl group (for example thiophene or pyridine), and an heterocycloalkyl group (for example morpholine). For example, each substituent of W may be independently selected from the group consisting of cyano, CF$_3$, an alkyl group optionally substituted with a heterocycle (such as an unsubstituted C1-C3 alkyl, for example methyl, ethyl, propyl), an aryl group (for example phenyl), an heteroaryl group (for example thiophene or pyridine), and an heterocycloalkyl group (for example morpholine). For example, each substituent of W may independently be an alkyl group optionally substituted with a heterocycle (such as an unsubstituted C1-C3 alkyl, for example methyl, ethyl and propyl). An example of W is 4-(C1-3)alkyl pyrimidin-2-yl.

The present disclosure discloses compounds wherein R1, R2, R3 and R4 may each be independently selected from the group consisting of hydrogen, halogen, an alkyl group optionally substituted with a heterocycle, an alkoxy group optionally substituted with a heterocycle and a solubilising group. For example, at least three of R1, R2, R3 and R4 are hydrogen. For example R3 and R4 are hydrogen, one of R1 and R2 is hydrogen and the other is selected from the group consisting of hydrogen, halogen, an alkyl group optionally substituted with a heterocycle and an alkoxy group optionally substituted with a heterocycle. For example, R1, R2, R3 and R4 are all hydrogen.

The present disclosure discloses compounds of the following formula (II) or a pharmaceutically salt thereof:

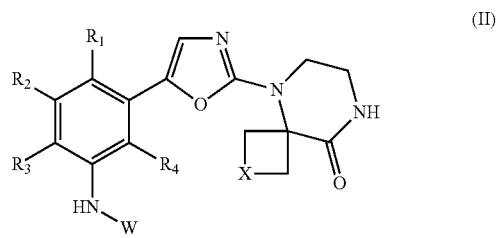

(II)

Wherein W, R1, R2, R3, R4 and X are as defined above. For example, W, R1, R2, R3, R4 are as defined above, X is (CH$_2$)n and n is 0, 1 or 2, such as 0. For example, in compounds of formula (II), at least three of R1 to R4, for example each one of R1 to R4 is hydrogen, W is a monosubstituted aryl or a monosubstituted heteroaryl, such as monosubstituted heteroaryl, X is (CH$_2$)n and n is 0, 1 or 2, such as 0.

The present disclosure discloses compounds of the following formula (III) or a pharmaceutically salt thereof:

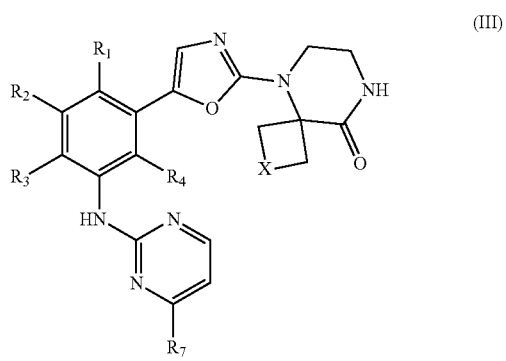

(III)

Wherein R1, R2, R3, R4 and X are as defined above and R7 is selected from the group consisting of:

hydrogen, cyano,

CF$_3$, halogen (selected from F, Cl, Br or I), an alkyl group, a cycloalkyl group, an alkoxy group, an aryl group, a heteroaryl group, a heterocycloalkyl group, a solubilising group and —NRR' group wherein R and R' are each independently selected from hydrogen or alkyl group.

For example, in compounds of formula (III), R1 to R4 and R7 are as defined above, X is (CH$_2$)n and n is 0, 1 or 2, such as 0. For example, R1 to R4 are as defined above, R7 is an alkyl group (such as C1-C3 alkyl, for example methyl, ethyl or propyl), X is (CH$_2$)n and n is 0, 1 or 2, such as 0. For example R3 and R4 are hydrogen, one of R1 and R2 is hydrogen and the other is selected from the group consisting of hydrogen, halogen, an alkyl group optionally substituted with a heterocycle and an alkoxy group optionally substituted with a heterocycle, X is (CH$_2$)n, n is 0, 1 or 2, such as 0, and R7 is C1-C3 alkyl, for example methyl, ethyl or propyl.

Unless otherwise specified, the below terms used herein are defined as follows.

As used herein, the term "alkyl" or "alkyl group" means a saturated straight chain or branched non-cyclic hydrocarbon. Unless otherwise indicated, alkyl groups may have from 1 to 10, such as from 1 to 6, or from 1 to 4 carbon atoms, for example from 1 to 3 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl and 3,3-diethylhexyl. Alkyl groups included in compounds of this invention may be unsubstituted or substituted with one or more (for example from one to five, such as one) substituents. An optional substituent may be a solubilising group.

As used herein, the term "aryl" or "aryl group" means a monocyclic or polycyclic-aromatic hydrocarbon radical. Unless otherwise indicated, aryl groups may have from 6 to 14 carbon atoms. Examples of suitable aryl groups include phenyl, tolyl, anthracenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more (for example from one to five, such as from one to four, for example one or two or three) substituents. The optional substituent may be a solubilising group.

The term "cycloalkyl" or "cycloalkyl group" means a saturated or partially unsaturated, monocyclic, fused bicyclic or bridged polycyclic ring assembly. This includes substituted or unsubstituted cycloalkyl groups. For example, cycloalkyl group may be a C3-C10 cycloalkyl group, such as C3 or C4 cycloalkyl group, such as a cyclopropyl, cyclobutyl, cyclopentyl, cyclohexyl, cycloheptyl or cyclooctyl group.

As used herein, the term "alkoxy" or "alkoxy group" refers to an alkyl group as defined above which is attached to another moiety by an oxygen atom. Examples of alkoxy groups include methoxy, isopropoxy, ethoxy, tert-butoxy.

As used herein, the term "heterocycle" refers collectively to heterocycloalkyl groups and heteroaryl groups.

As used herein, the term "heterocycloalkyl" or "heterocycloalkyl group" means a monocyclic or polycyclic group having at least one (for example from one to five, such as one or two or three or four) heteroatom selected from O, N or S, and which may be saturated or unsaturated, but is not aromatic. A heterocycloalkyl may have from 2 to 11 carbon atoms. Examples of heterocycloalkyl groups including: piperidinyl, piperazinyl, N-methylpiperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 ring atoms. Preferred 3 to 7 membered monocyclic heterocycloalkyl groups have 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be unsubstituted or substituted with one or more (such as from one to four, such as one or two) substituents. In addition, the point of attachment of a heterocyclic ring to another group may be at either a carbon atom or a heteroatom of a heterocyclic ring.

As used herein, the term "heteroaryl" or "heteroaryl group" means a monocyclic or polycyclic heteroaromatic ring comprising carbon atom ring members and one or more heteroatom ring members (such as, for example, oxygen, sulfur or nitrogen). Typically, heteroaryl groups may have from 5 to 14, such as from 5 to 8 ring members. Typically, a heteroaryl group has from 1 to 5, such as one or two or three or four, heteroatom ring members. Typically may have from 1 to about 14 carbon atom ring members. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzo(b)thienyl. A heteroatom may be substituted with a protecting group known to those of ordinary skill in the art, for example, the hydrogen on nitrogen may be substituted with a tert-butoxycarbonyl group. Heteroaryl groups may be unsubstituted or substituted with one or more substituents. In addition, nitrogen or sulfur heteroatom ring members may be oxidized. The heteroaromatic ring may be a 5-8 membered monocyclic heteroaryl ring. The point of attachment of a heteroaromatic or heteroaryl ring to another group may be at either a carbon atom or a heteroatom of the heteroaromatic or heteroaryl rings.

As used herein the term "substituent" or "substituted" means that a hydrogen radical on a compound or group is replaced with any desired group that is substantially stable to reaction conditions in an unprotected form or when protected using a protecting group. Examples of substituents are those found in the exemplary compounds and embodiments disclosed herein, as well as halogen, alkyl or aryl groups as defined above, hydroxyl, alkoxy as defined above, nitro, thiol, heterocycloalkyl groups, heteroaryl groups, cyano, cycloalkyl groups as defined above, as well as a solubilising group, —NRR', —NR—CO—R', —CONRR', —SO$_2$NRR' group wherein R and R' are each independently hydrogen or alkyl as defined above. Examples of substituents are halogen, C1-C10 unsubstituted alkyl, C6-C14 unsubstituted aryl, hydroxyl, C1-C10 unsubstituted alkoxy, nitro, thiol, unsubstituted 3-7 membered heterocycloalkyl, unsubstituted 3-7 membered heteroaryl, cyano, C1-C10 unsubstituted cycloalkyl, a solubilising group, —NRR', —NR—CO—R', —CONRR', —SO$_2$NRR' group wherein R and R' are each independently hydrogen or C1-C10 unsubstituted alkyl.

As used herein, the term "solubilising" group means a group which has a hydrophilic character sufficient to improve or increase the water-solubility of the compound in which it is included, as compared to an analog compound that does not include the group. The hydrophilic character can be achieved by any means, such as by the inclusion of functional groups that ionize under the conditions of use to form charged moieties (e.g., carboxylic acids, sulfonic acids, phosphoric acids, amines, etc.); groups that include permanent charges (e.g., quaternary ammonium groups); and/or heteroatoms or heteroatomic groups.

Examples of "heteroatomic groups" are N—(CH$_2$)zR", N—(CH$_2$)z-C(O)R", N—(CH$_2$)z-C(O)OR", N—(CH$_2$)z-S(O)$_2$R", N—(CH$_2$)z-S(O)$_2$OR", N—(CH$_2$)z-C(O)NR"R"', where z is an integer ranging from 0 to 6, such as 0 or 1 or 2 or 3 or 4 or 5 or 6, R" and R"' are each independently selected from the group consisting of:
hydrogen,
a C1-C10 alkyl group which is optionally substituted with one or more hetereoatoms such as halogen (selected from F, a, Br or I), oxygen, and nitrogen,
a C1-C10 alkoxy group,
an unsubstituted aryl, and
an unsubstituted heteroaryl group.

The solubilising group may be a moiety having one of the following structures:

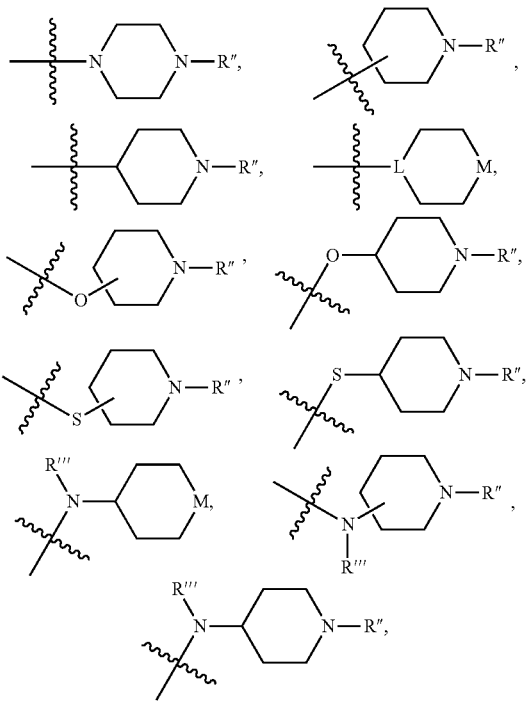

wherein
L is selected from the group consisting of CH and N,
M is selected from the group consisting of —CH(R")—, —CH$_2$—, —O—, —S—, —NH—, —N(—(CH$_2$)z-R")—, —N(—(CH$_2$)z-C(O)R")—, —N(—(CH$_2$)z-C(O)OR")—, —N(—(CH$_2$)z-S(O)$_2$R"')—, —N(—(CH$_2$)z-S(O)$_2$OR")— and —N(—(CH$_2$)z-C(O)NR"R"')—, where z is an integer ranging from 0 to 6, R" and R"' are each independently selected from:
hydrogen,
a C1-C10 alkyl group which is optionally substituted with one or more hetereoatoms such as halogen (selected from F, a, Br or I), oxygen, and nitrogen,
a C1-C10 alkoxy group,
an unsubstituted aryl, and
an unsubstituted heteroaryl, or the group —NR"R"' is a group —NRR' group wherein R$^a$ and R$^b$ are each independently selected from hydrogen or unsubstituted alkyl;
with the proviso that L and M are not both simultaneously CH and CH$_2$, respectively.

Examples of solubilising groups are morpholinyl, piperidinyl, pyrrolidinyl, N—(C1-C6)alkyl piperidinyl, in particular N-methyl piperidinyl and N-ethyl piperidinyl, N-(4-piperidinyl)piperidinyl, 4-(l-piperidinyl)piperidinyl, 1-pyrrolidinylpiperidinyl, 4-morpholinopiperidinyl, 4-(N-methyl-l-piperazinyl)piperidinyl, piperazinyl, N—(C1-C6) alkylpiperazinyl, in particular N-methyl piperazinyl and N-ethyl piperazinyl, N—(C3-C6)cycloalkyl piperazinyl, in particular N-cyclohexyl piperazinyl, pyrrolidinyl, N—(C1-C6)alkyl pyrrolidinyl, in particular N-methyl pyrrolidinyl and N-ethyl pyrrolidinyl, diazepinyl, N—(C1-C6)alkyl azepinyl, in particular N-methyl azepinyl and N-ethyl azepinyl, homopiperazinyl, N-methyl homopiperazinyl, N-ethyl homopiperazinyl, imidazolyl.

The compounds of formula (I) may be used in the form of salts derived from pharmaceutically acceptable inorganic or organic adds. Unless otherwise indicated, "pharmaceutically acceptable salt" refers to a salt prepared by combining a compound of formula (I) with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid. Suitable pharmaceutically acceptable acid addition salts of the compounds of the present invention when possible include those derived from inorganic adds, such as hydrochloric, hydrobromic, hydrofluoric, boric, fluoroboric, phosphoric, metaphosphoric, nitric, carbonic, sulfonic, and sulfuric acids, and organic adds such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic adds. Suitable organic acids generally include, for example, aliphatic, cycloaliphatic, aromatic, araliphatic, heterocyclic, carboxylic, and sulfonic classes of organic adds. Specific examples of suitable organic adds include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, β-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate. Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts. Organic salts may be made from secondary, tertiary or quaternary amine salts, such as tromethamine, diethylamine, /\/,/\/'-dibenzylethylenediamine, chloroprocaine, choline, diethanolamine, ethylenediamine, meglumine (/\/-methylglucamine), and procaine. Basic nitrogen-containing groups may be quaternized with agents such as lower alkyl (CrCe) halides (e.g., methyl, ethyl, propyl, and butyl chlorides, bromides, and iodides), dialkyl sulfates (i.e., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others. Hemisalts of acids and bases may also be formed, for example, hemisulfate and hemicalcium salts.

Unless otherwise indicated, the language "compounds of formula (I)" include all forms of the compound of formula I, including hydrates, solvates isomers, crystalline and non-crystalline forms, isomorphs, polymorphs, and metabolites thereof. For example, the compounds of formula (I), or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. Stereoisomers of the compounds of formula (I) include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Unless otherwise indicated, the language "compounds of formula (I)" include the tautomeric forms of compounds. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form is dependent on the various substituents on the molecule as well as the particular crystallization technique used to isolate a compound.

The compounds of the present invention may be prepared using the general protocols as follows:

General Synthetic Procedures

Compounds of the invention can be prepared by several methods including methods outlined in Schemes 1-4, wherein the substituents are as defined in formula (I) above, except where further noted. The synthetic methods described below are merely exemplary, and the compounds of the invention may be synthesized by alternate routes as appreciated by persons of ordinary skill in the art.

Piperazinones (2) (Scheme 1) were prepared by reacting ethylene diamine with 2-bromo ester (1) using the method described by A. Benjahad et al (*Tetrahedron Letters*, (1994), 9545-9548).

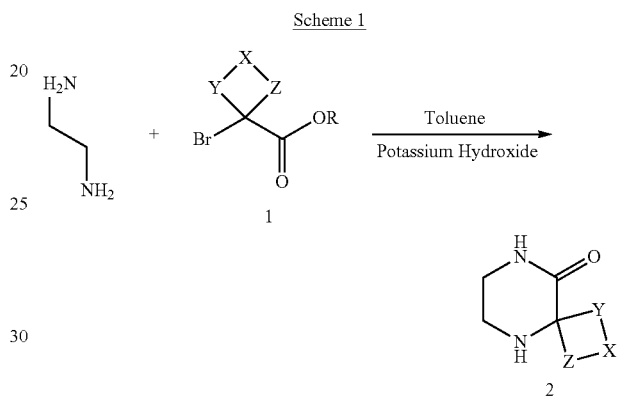

The piperazinones (2) may alternatively be prepared via N-Nosyaziridine (4) according to the protocol outlined in Scheme 2. N-Nosyaziridine intermediate (4) is prepared from 2-chloroethylamine hydrochloride by first reacting with p-nitrosulfonyl chloride to give the N-Nosylamine (3) which is subsequently cyclised with potassium hydroxide to afford (4) using a method adapted from Iwaki et al (*Bioorganic & Medicinal Chemistry Letters*, (2012), 2798-2802). Ring-opening with an amino acid ethyl ester hydrochloride (5) gives the acyclic aminoester (6) which is cyclised in 2 steps: N-deprotection with thiophenol then heating to afford piperazinones (2) as described by Maligres et al (*Tetrahedron Letters*, (1997), 5253-5256).

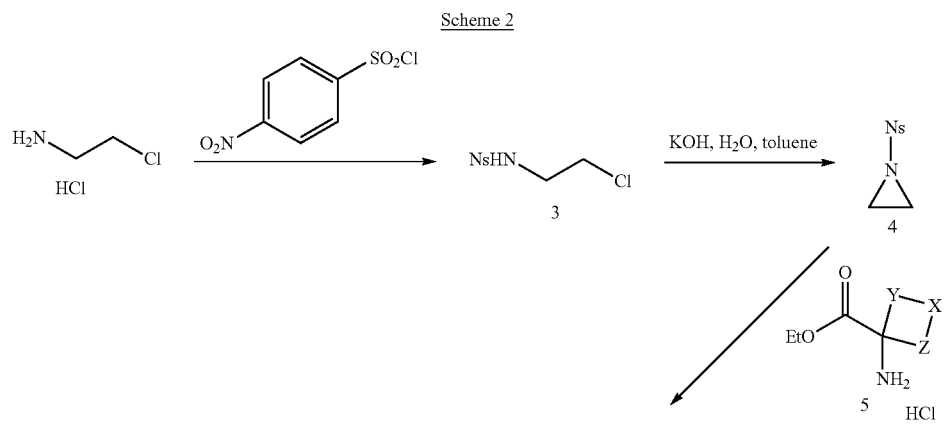

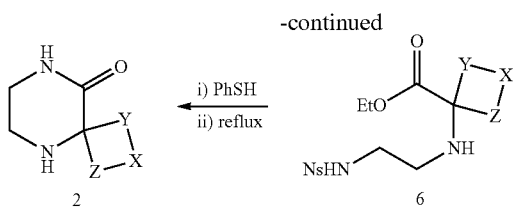

Aromatic aldehydes (7) (Scheme 3) were reacted with p toluenesulfonylmethyl isocyanide (TosMIC) to prepare the corresponding 5-arylsubstituted oxazoles (8) using the method of Van Leusen et al (*Tetrahedron Letters*, (1972), 2369-2372). The non-commercial aldehydes (7) were prepared using literature methods. Deprotonation of the oxazole moiety (8) by a suitable organic base such as lithium hexamethyldisilazide (LiHMDS) and subsequent electrophilic chlorination was used to prepare the 2-chlorooxazole compounds (9). This allowed access to compounds (10) by substitution of the chloride by substituted piperazinones (2). This substitution was performed either by heating in the presence of solvent such as isopropanol or heating under solvent-free conditions. In certain cases and in the presence of solvent, compounds (10) can be obtained by using an acid such as hydrochloric acid. Nitro compound (10) is reduced to form the corresponding aniline (11). Preferably, the reduction reaction is performed in the presence of hydrogen with a catalyst, such as a palladium on carbon 10% by wt. Compounds (11) were used to prepare further analogues (12) of formula (I) by a direct nucleophilic displacement reaction in the presence of a suitable solvent such as alcohol and with heating in elevated temperature, where X of W—X can be F, I, Br or Cl. Presence of an acid such as hydrochloric acid may or may not be necessary to drive the reaction to completion or to obtain improved yields. In certain cases compounds (12) can be obtained by using known metal-catalysed N-arylation protocols with a suitable combination of ligand and inorganic base.

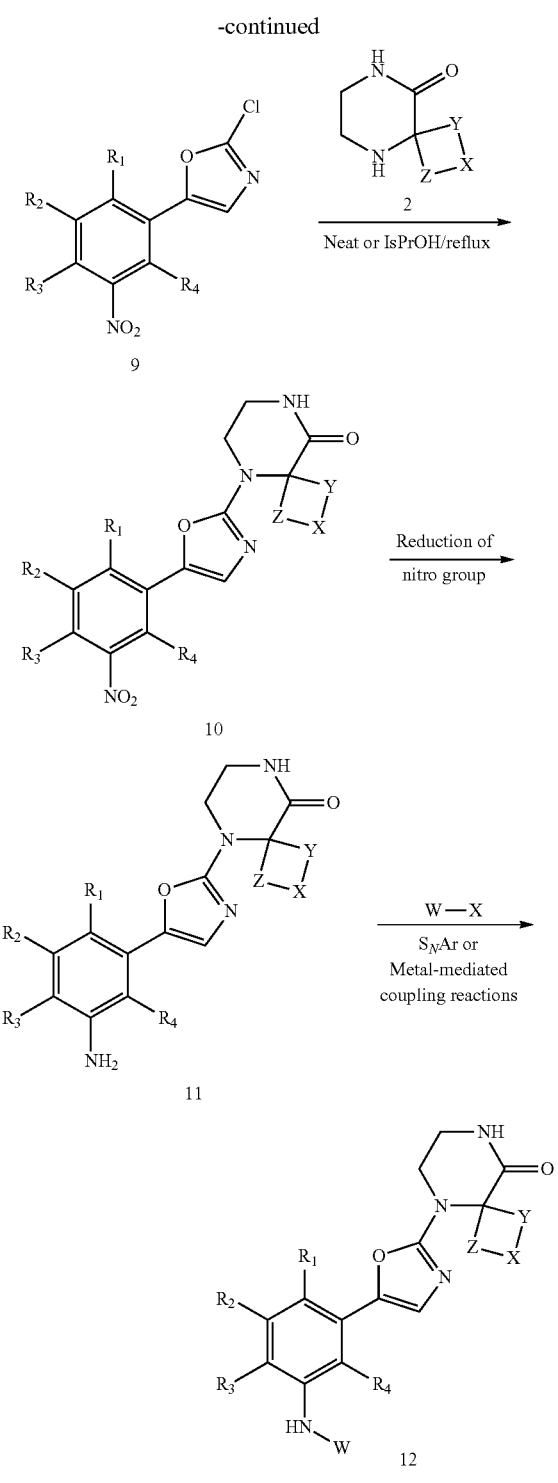

Following the reaction scheme depicted in Scheme 4, compounds (12) of formula (I) were obtained by using the same protocols described above.

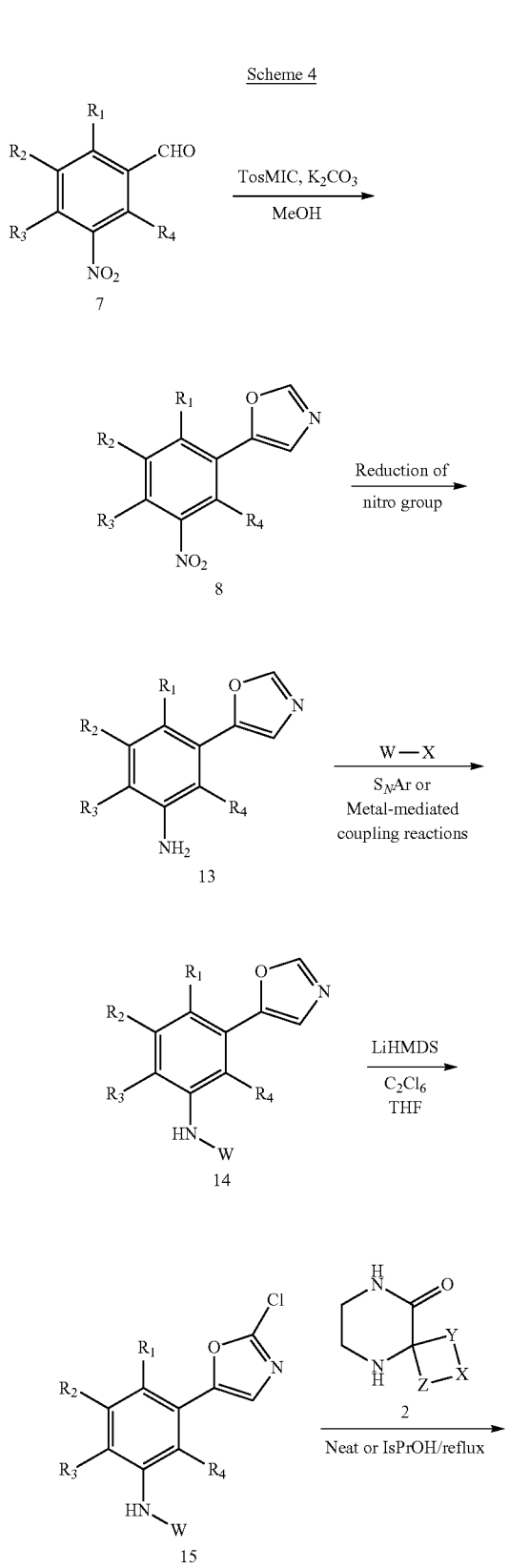

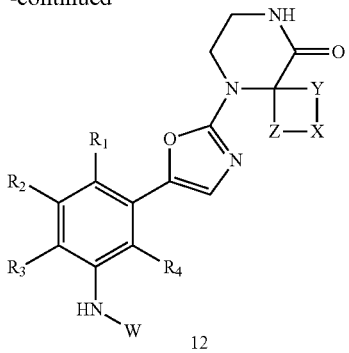

In a second aspect, the present disclosure discloses a pharmaceutical composition comprising a compound of formula (I) as defined above, such as a compound of formula (II) or (III), or a pharmaceutically acceptable salt thereof, and a pharmaceutically acceptable excipient and/or carrier. In the pharmaceutical composition, a compound of formula (I) may be the sole pharmaceutically active ingredient or it may be combined with one or more distinct pharmaceutically active ingredients.

Suitable carriers and excipients are widely known in the art and are commonly used for example to facilitate the processing of the active compounds into preparations which can be used pharmaceutically. Further details on techniques for formulation and administration may be found in the latest edition of Remington's Pharmaceutical Sciences (Maack Publishing Co., Easton, Pa.).

Various forms of excipients can be used depending on the desired mode of administration and some of them can improve or tailor the effectiveness of the active compound, e.g. by promoting a release profile rendering this active compound overall more effective for the treatment desired. The pharmaceutical compositions of the invention are suitable to be administered in various forms, for example in an injectable, pulverizable or ingestible form, for example via the intramuscular, intravenous, subcutaneous, intradermal, oral, topical, rectal, vaginal, ophthalmic, nasal, transdermal or parenteral route.

The pharmaceutical composition presently disclosed may be intended for oral administration. In this case, the composition may be formulated as tablets, pills, dragees, capsules, liquids, gels, syrups, slurries, suspensions, and the like, for ingestion by the patient.

The compositions presently disclosed may be a pharmaceutical or cosmetic composition. They may be intended for topical administration. Such compositions may be presented in the form of a gel, paste, ointment, cream, lotion, liquid suspension, aqueous-alcoholic or oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions may be prepared according to standard methods.

The compositions presently defined may comprise any ingredient commonly used in dermatology and cosmetics. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, perfumes, fillers, screening agents, bactericides, odor absorbers and coloring matter. As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances. Emulsifiers which can be used in the invention include, for example, glycerol stearate, polysorbate 60 and the PEG-6/PEG-32/glycol stearate mixture. Hydrophilic gelling agents which can be used in the invention include, for example, carboxyvinyl polymers (carbomer), acrylic copolymers such as acrylate/alkylacrylate copolymers, polyacrylamides, polysaccharides such as hydroxypropylcellulose, clays and natural gums. Lipophilic gelling agents which can be used in the invention include, for example modified clays such as bentones, metal salts of fatty acids such as aluminum stearates and hydrophobic silica, or alternatively ethylcellulose and polyethylene. As hydrophilic active agents, proteins or protein hydrolysates, amino acids, polyols, urea, allantoin, sugars and sugar derivatives, vitamins, starch and plant extracts, in particular those of Aloe Vera may be used. As lipophilic active, agents, retinol (vitamin A) and its derivatives, tocopherol (vitamin E) and its derivatives, essential fatty acids, ceramides and essential oils may be used. These agents add extra moisturizing or skin softening features when utilized. In addition, a surfactant can be included in the composition so as to provide deeper penetration of the compound capable of depleting mast cells, such as a tyrosine kinase inhibitor. Among the contemplated ingredients, one may chose penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents. Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis: An Electromeric Study," J. Ivest. Dermatol., V. 60, (1973), pp. 263-69), lauryl amine oxide (Johnson et al, U.S. Pat. No. 4,411,893), azone (Rajadhyaksha, U.S. Pat. Nos. 4,405,616 and 3,989,816) and decylmethyl sulfoxide (Sekura, D. L and Scala, J., "The Percutaneous Absorption of Alkylmethyl Sulfides," Pharmacology of the Skin, Advances In Biology of Skin, (Appleton-Century Craft) V. 12, (1972), pp. 257-69). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects," Surfactant Science Series, V. 16, Reiger, M. M. ed. (Marcel Dekker, Inc.), (1987), pp. 195-210). Chemical enhancers may also be co-solvents. These materials are absorbed topically relatively easily, and, by a variety of mechanisms, achieve permeation enhancement for some drugs. Ethanol (Gale et al, U.S. Pat. No. 4,615,699 and Campbell et al., U.S. Pat. Nos. 4,460,372 and 4,379,454), dimethyl sulfoxide (U.S. Pat. No. 3,740,420 and U.S. Pat. No. 3,743,727, and U.S. Pat. No. 4,575,515), and glycerin derivatives (U.S. Pat. No. 4,322,433) are a few examples of compounds which have shown an ability to enhance the absorption of various compounds.

The pharmaceutical compositions presently disclosed can also be intended for administration with aerosolized formulation to target areas of a patient's respiratory tract. Devices and methodologies for delivering aerosolized bursts of a formulation of a drug is disclosed in U.S. Pat. No. 5,906,202. Formulations are preferably solutions, e.g. aqueous solutions, ethanolic solutions, aqueous/ethanolic solutions, saline solutions, colloidal suspensions and microcrystalline suspensions. For example aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs. Suitable devices for the administration of the present compounds to a patient's respiratory tract are discussed for example in U.S. Pat. No. 5,556,611:

liquid gas systems (a liquefied gas is used as propellant gas e.g. low-boiling FCHC or propane, butane in a pressure container), suspension aerosol (the active substance particles are suspended in solid form in the liquid propellant phase), pressurized gas system (a compressed gas such as nitrogen, carbon dioxide, dinitrogen monoxide, or air is used.

Thus, the pharmaceutical composition presently disclosed is made in that the active substance is dissolved or dispersed in a suitable nontoxic medium and said solution or dispersion atomized to an aerosol, i.e. distributed extremely finely in a carrier gas. This is technically possible for example in the form of aerosol propellant gas packs, pump aerosols or other devices known per se for liquid misting and solid atomizing which in particular permit an exact individual dosage. Therefore, to the present disclosure also discloses aerosol devices comprising a compound as defined above and such a formulation, preferably with metered dose valves.

The pharmaceutical compositions presently disclosed can also be intended for intranasal administration. In this regard, pharmaceutically acceptable carriers for administering the compound to the nasal mucosal surfaces will be readily appreciated by the ordinary artisan. These carriers are described in the Remington's Pharmaceutical Sciences" 16$^{th}$ edition, (1980), Ed. By Arthur Osol, the disclosure of which is incorporated herein by reference.

For administration via the upper respiratory tract, the composition can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration. Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about 150 mg per 100 ml of carrier. Other ingredients, such as known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions, various devices are available in the art for the generation of drops, droplets and sprays.

A premeasured unit dosage dispenser including a dropper or spray device containing a solution or suspension for delivery as drops or as a spray is prepared containing one or more doses of the drug to be administered. Also disclosed is a kit containing one or more unit dehydrated doses of a compound of formula (I) as presently disclosed, together with any required salts and/or buffer agents, preservatives, colorants and the like, ready for preparation of a solution or suspension by the addition of a suitable amount of water.

Another aspect of the present disclosure is directed to a compound of formula (I) as defined above, such as a compound of formula (II) or (III), or a pharmaceutically acceptable salt thereof, for use as a medicament.

The compounds of formula (I) or pharmaceutically salts thereof as presently disclosed (also jointly referred to as "compounds of formula (I)") are endowed with Syk tyrosine kinase inhibiting activity. In particular, they may inhibit (thereby regulating) the signal transduction mediated by Syk.

Accordingly, in one aspect the present disclosure discloses a method for treating a disease or disorder associated with unregulated or deregulated Syk activity, said method comprising administering an effective amount of a compound of formula (I) to a subject (such as a human or animal subject) in need of such treatment. For example, the present disclosure discloses a method for treating a disease or disorder associated with signal transduction mediated by SYK, the present disclosure discloses a method for treating a disease or disorder associated.

Effective amounts of the compounds of formula (I) are generally comprised between 0.1 mg and 2 g of the compound per day and per kilogram of body weight.

In another aspect, the present disclosure discloses a method for modulating, regulating, and/or inhibiting, in cells, the signal transduction mediated by Syk protein kinase. Said method comprises administering to cells at least one compound of formula (I) as defined above, such as a compound of formula (II) or (III), or a pharmaceutically acceptable salt thereof.

The present disclosure discloses the use of at least one compound of formula (I) or a pharmaceutically acceptable salt thereof, for the in vitro or in vivo selective inhibition of Syk.

The methods presently disclosed may be for treating a hematological, an inflammatory, an autoimmune, a proliferative, a metabolic, an allergic and/or degenerative disease or disorder in a patient.

In one embodiment, said subject or patient has been diagnosed as having hematological disorders, allergic disorders, metabolic disorders, inflammatory disorders, autoimmune disorders and/or proliferative disorders.

Diseases and disorders known to be associated with unregulated or deregulated signal transduction mediated by Syk are for example:

hematological disorders such as Non-Hodgkin Lymphoma and leukemia including Diffuse large B-cell lymphoma (DLBCL) Follicular lymphoma (FL), Mantle cell lymphoma (MCL), B-cell chronic lymphocytic leukemia (B-CLL)/small lymphocytic lymphoma (SLL), Waldenstrom's macroglbulinemia (WM), Marginal zone lymphoma (MZL), Burkitt lymphoma and peripheral T-cell lymphomas (PTCL), as well as multiple myeloma (MM), myelodysplatic syndrome (MDS), myelodysplasia with myelofibrosis, neoplastic diseases such as mastocytosis, solid tumours including head and neck cancer, hepatocellular carcinoma, and human gastrointestinal disorders.

metabolic diseases such diabetes mellitus and its chronic complications, obesity, diabetes type II, hyperlipidemias and dyslipidemias, atherosclerosis; hypertension and cardiovascular disease.

allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation.

bone resorption (osteoporosis).

angiogenesis inflammatory diseases such as rheumatoid arthritis, conjunctivitis, rheumatoid spondylitis, osteoarthritis, gouty arthritis and other arthritic conditions.

autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis and T-cell mediated autoimmune diabetes.

graft-versus-host disease or graft rejection for allogeneic hematopoetic cell transplantation for the treatment of leukemia and lymphoma, cardiac allograft and in any organ transplantation such as kidney, pancreas, liver, and lung.

Other autoimmune diseases embraced by the invention include active chronic hepatitis and chronic fatigue syndrome.

vasculitis.

viral infection.

fungal infection.

bacterial infection.

CNS disorders such as Nasu-Hakola disease, psychiatric disorders, migraine, pain, memory loss and nerve cells degeneracy. More particularly, the method according to the invention is useful for the treatment of the following disorders: depression including dysthymic disorder, cyclothymic disorder, bipolar depression, severe or "melancholic" depression, atypical depression, refractory depression, seasonal depression, anorexia, bulimia, premenstrual syndrome, post-menopause syndrome, other syndromes such as mental slowing and loss of concentration, pessimistic worry, agitation, self-deprecation, decreased libido, pain including, acute pain, postoperative pain, chronic pain, nociceptive pain, cancer pain, neuropathic pain, psychogenic pain syndromes, anxiety disorders including anxiety associated with hyperventilation and cardiac arrhythmias, phobic disorders, obsessive-compulsive disorder, post-traumatic stress disorder, acute stress disorder, generalized anxiety disorder, psychiatric emergencies such as panic attacks, including psychosis, delusional disorders, conversion disorders, phobias, mania, delirium, dissociative episodes including dissociative amnesia, dissociative fugue and dissociative identity disorder, depersonalization, catatonia, seizures, severe psychiatric emergencies including suicidal behaviour, self-neglect, violent or aggressive behaviour, trauma, borderline personality, and acute psychosis, schizophrenia including paranoid schizophrenia, disorganized schizophrenia, catatonic schizophrenia, and undifferentiated schizophrenia, neurodegenerative diseases including Alzheimer's disease, Parkinson's disease, Huntington's disease, the prion diseases, Motor Neurone Disease (MND), and Amyotrophic Lateral Sclerosis (ALS).

Cerebral ischemia

Retinal ischemia

Ischemic stroke

Fibrosis.

Hematological malignancies may be non-Hodgkin lymphoma (NHL) including B-CLL/SLL, DLBCL, FL, MCL and WM, peripheral T-cell lymphoma and myelodysplastic syndromes (MDS). Proliferative disorder may be cancer. Autoimmune disorders may be multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, atopic dermatitis and/or proliferative glomerulonephritis. Allergic diseases may be asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and/or blood sucking parasitic infestation. Neurologic diseases may be Huntington's disease, schizophrenia, Parkinson's disease and/or Alzheimer's disease.

In one particular embodiment, the methods presently disclosed may be for preventing or treating a disease or disorder selected form rheumatoid arthritis, asthma, multiple sclerosis, atopic dermatitis, Crohn's disease, interstitial cystitis, ankylosing spondylitis, chronic obstructive pulmonary disease, psoriasis, mastocytosis, B-cell malignancies, colorectal carcinoma, lung cancer, gastric carcinoma, glioblastoma, gastrointestinal stromal tumor (GIST), melanoma, breast cancer, triple negative breast cancer, gastric carcinoma, oesogastric carcinoma, pancreatic cancer, prostate cancer, multiple myeloma, T-cell lymphoma, head and neck cancer, hepatocellular carcinoma, Hodgkin lymphoma, ischemic hepatitis, hepatitis B, amyotrophic lateral sclerosis (ALS), Parkinson's disease, muscular dystrophy (de Duchene), progressive supranuclear palsy (PSP), cerebral ischemia, addiction, cocaine addiction, depression, mood disorders associated to major depression or dysthymic disorder, and Alzheimer's disease.

A compound of formula (I), such as a compound of formula (II) or (III), or a pharmaceutically acceptable salt thereof may be used for treating a disease or disorder disclosed above such as hematological disorders, proliferative disorders, autoimmune disorders, metabolic disorders, inflammatory disorders and/or allergic disorders.

In the methods presently disclosed, the compound of formula (I) or a pharmaceutically acceptable salt thereof, may be used as sole active pharmaceutical ingredient or in combination with another active pharmaceutical ingredient.

The present disclosure discloses a method for preventing or treating a disease or disorder selected form hematological disorders, proliferative disorders, metabolic disorders, inflammatory disorders, autoimmune disorders and allergic disorders, that method comprising simultaneously or sequentially administering to a human or animal subject in need thereof at least one compound of formula (I) or a pharmaceutically acceptable salt thereof in combination with another active pharmaceutical ingredient, in sufficient amounts to provide a therapeutic effect.

The present disclosure discloses a pharmaceutical composition comprising a compound of formula (I) such as a compound of formula (II) or (III), or a pharmaceutically acceptable salt thereof, and another active pharmaceutical agent as a combined preparation for sequential, simultaneous or separate use in the treatment of a disease or disorder selected from the group consisting of hematological disorders, proliferative disorders, autoimmune disorders, inflammatory disorders, and allergic disorders.

The present disclosure discloses the use of a compound of formula (I) such as a compound of formula (II) or (III), or a pharmaceutically acceptable salt thereof optionally in combination with another pharmaceutically active agent, for the manufacture of a medicament for the treatment of a a disease or disorder selected from the group consisting of a hematological disorder, a proliferative disorder, a metabolic disorder, an autoimmune disorder, an inflammatory disorder, and an allergic disorder.

Although methods and uses disclosed above refer to a compound of formula (I), such as a compound of formula (II) or (III), or a pharmaceutically acceptable salt thereof, whenever technically compatible they are to be understood to equally refer to pharmaceutical compositions including the same compounds.

The invention is now illustrated by Examples which represent currently preferred embodiments which make up a part of the invention but which in no way are to be used to limit the scope of it.

Examples of Compound Synthesis

The invention will be more fully understood by reference to the following preparative examples, but they should not be construed as limiting the scope of the invention. General: All chemicals used were commercial reagent grade products. Solvents were of anhydrous commercial grade and were used without further purification. The progress of the reactions was monitored by thin layer chromatography using precoated silica gel 60F 254, Merck TLC plates, which were visualized under UV light. Multiplicities in $^1$H NMR spectra are indicated as singlet (s), broad singlet (br s), doublet (d), triplet (t), quadruplet (q), and multiplet (m) and the NMR spectrum were performed either on a Bruker 300 or 400 MHz spectrometer. Liquid chromatography-Mass Spectrometry (LCMS) was run on an Ultra-high performance liquid chromatography (UPLC) ACQUITY Waters instrument coupled to a TQD mass spectrometer. The gradient used was: starting at t=0.0 min with 5% of $CH_3CN$+0,1% Formic acid in Water+0,1% Formic acid until t=0.5 min; then a linear gradient from t=0.5 min to t=7.0 min reaching 100% $CH_3CN$+0,1% Formic acid; then staying at this state from t=7.0 min until t=10.0 min. The column used was a Waters HSS C18 1.8 μm, 2.1×50 mm. The detection instrument used was the triple quadrupole mass spectrometer (TQD) using electrospray ionisation (ESI) in positive mode. Chemical names were generated using ChemDraw Ultra Version 7.0.1

Abbreviations

CDCl$_3$ Deuterochloroform
Conc. HCl Concentrated hydrochloric acid (37%)
Cs$_2$CO$_3$ Cesium carbonate
DCM Dichloromethane
DMSO-d$_6$ Hexadeuterodimethyl sulfoxide
EtOAc Ethyl acetate
EtOH Ethanol
Et$_3$N Triethylamine
Fe(acac)$_3$ Tris(acetylacetonato) iron(III)
h Hour(s)
iPrOH 2-Propanol
K$_2$CO$_3$ Potassium carbonate
KOH Potassium hydroxide
LiHMDS Lithium bis(trimethylsilyl)amide
MeCN Acetonitrile
MeOH Methanol
MgSO$_4$ Magnesium sulfate
Mins Minutes
NaCl Sodium Chloride
Na$_2$CO$_3$ Sodium carbonate
NaHCO$_3$ Sodium hydrogencarbonate
Ns Nosyl or p-nitrophenylsulfonyl
Pd$_2$(dba)$_3$ Tris(dibenzylideneacetone)dipalladium(0)
Pd(PPh$_3$)$_4$ Tetrakis(triphenylphosphine)palladium(0)
RT Room temperature
SiO$_2$ Silica gel
TosMIC p-Toluenesulfonylmethyl isocyanide
THF Tetrahydrofuran
tR Retention time
Xantphos 4,5-Bis(diphenylphosphino)-9,9-dimethylxanthene Example 001

Synthetic Approach of Compound 001

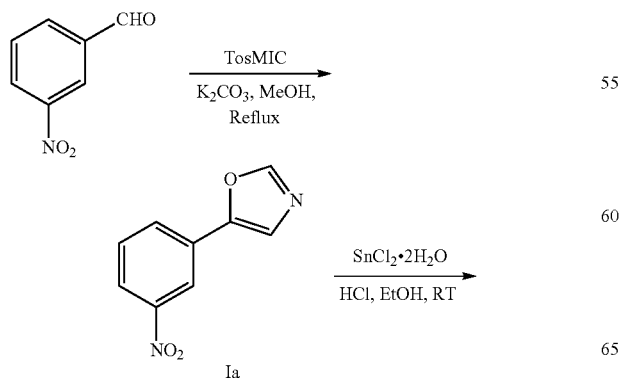

-continued

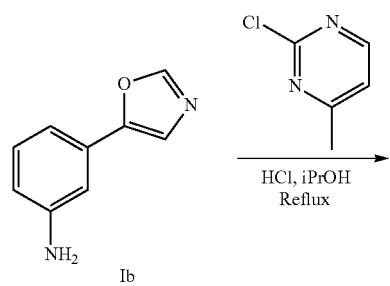

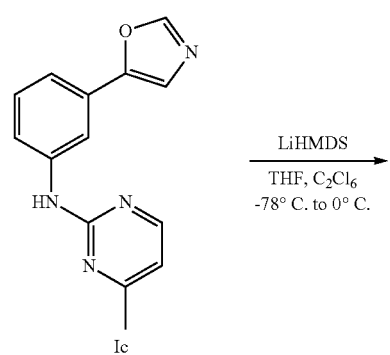

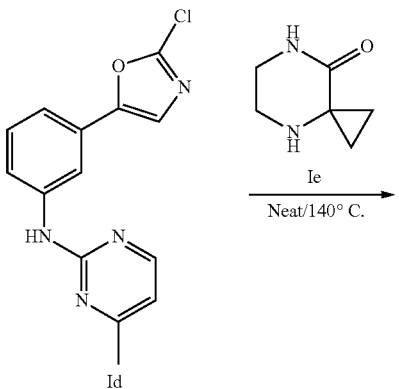

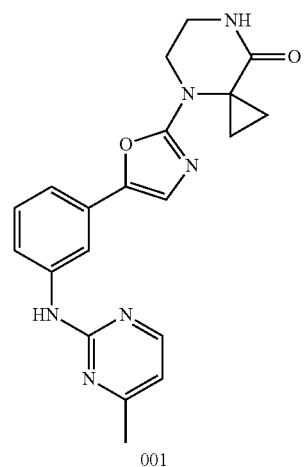 [SMILES: Cc1ccnc(Nc2cccc(-c3cnc(N4CCNC(=O)C45CC5)o3)c2)n1]

Preparation of 4,7-Diaza-spiro[2.5]octan-8-one (Ie)

Synthetic Approach of Intermediate (Ie)

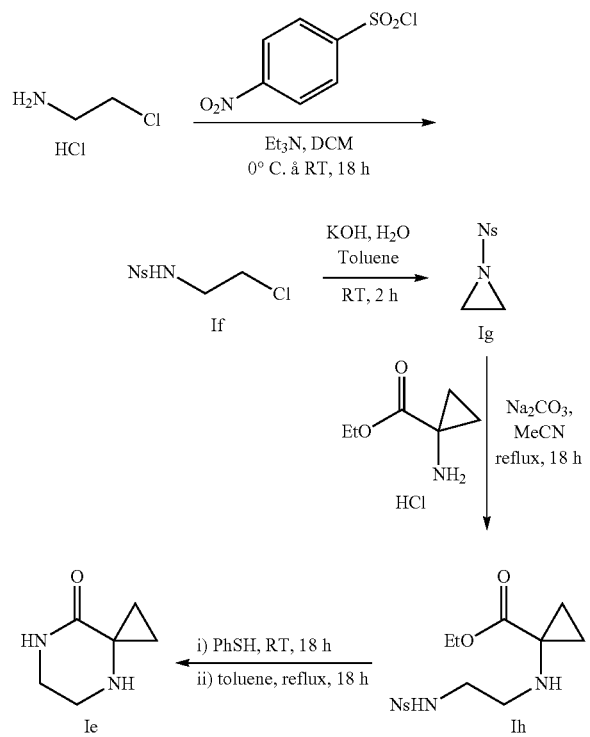

Preparation of
N-(2-Chloro-ethyl)-4-nitro-benzenesulfonamide (If)

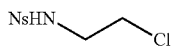

A stirred solution of 2-chloroethylamine hydrochloride (1.00 g, 8.62 mmol) and Et$_3$N (3.60 ml, 25.9 mmol) in dry DCM (25 ml) at 0° C. was treated with a solution of nosyl chloride (1.91 g, 8.62 mmol) in dry DCM (25 ml) dropwise. On complete addition, the solution was warmed to ambient temperature and stirred overnight. The solution was evaporated and the residue purified by column chromatography (SiO$_2$, 20% EtOAc to 30% EtOAc in cyclohexane) to afford the title compound as a white solid (2.03 g, 89%). $^1$H NMR (400 MHz, DMSO-d$_6$) δ 8.45-8.38 (m, 3H), 8.09-8.04 (m, 2H), 3.59 (t, J=6.0 Hz, 2H), 3.17 (s, 2H).

Preparation of 1-(4-Nitro-benzenesulfonyl)-aziridine (Ig)

Intermediate Ig was prepared according to the method of Iwaki et al, *Bioorganic & Medicinal Chemistry Letters* (2012), 2798-2802. A stirred slurry of If (2.00 g, 7.56 mmol) in toluene (100 ml) was treated with a solution of KOH (2.54 g, 45.3 mmol) in water (12 ml) in one portion then stirred at ambient temperature for 3 h. The solution was diluted with EtOAc and the organics separated, washed with saturated aqueous NaCl, dried (MgSO$_4$), filtered and evaporated to afford the title compound as a pale yellow solid (1.41 g, 82%). $^1$H NMR (400 MHz, CDCl$_3$) δ 8.47-8.26 (m, 2H), 8.24-8.10 (m, 2H), 2.48 (s, 4H).

Preparation of 1-[2-(4-nitro-benzenesulfonylamino)-ethylamino]-cyclopropane carboxylic acid ethyl ester (Ih)

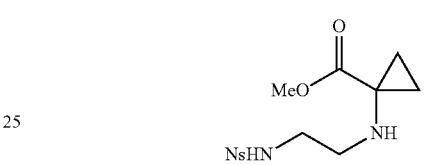

A mixture of the Ns-aziridine Ig (6.89 g, 30.2 mmol), 1-amino-cyclopropanecarboxylic acid ethyl ester hydrochloride (5.00 g, 30.2 mmol) and Na$_2$CO$_3$ (3.20 g, 30.2 mmol) in dry acetonitrile (120 ml) was heated to reflux for 3 h. The mixture was cooled, filtered and evaporated. The residue was purified by column chromatography (SiO$_2$, 5% acetone to 10% acetone in DCM) to afford the title compound as a pale yellow solid (6.58 g, 61%). $^1$H NMR (400 MHz, DMSO-d$_6$) δ 8.41 (d, J=8.8 Hz, 2H), 8.04 (d, J=8.8 Hz, 2H), 7.84 (br s, 1H), 4.02 (q, J=7.1 Hz, 2H), 2.84 (s, 2H), 2.72-2.58 (m, 3H), 1.14 (t, J=7.1 Hz, 3H), 1.07 (dd, J=7.0, 3.7 Hz, 2H), 0.81 (dd, J=7.0, 3.8 Hz, 2H).

Preparation of 4,7-Diaza-spiro[2.5]octan-8-one (Ie)

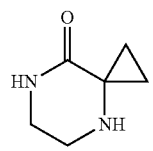

Prepared largely according to the method of Maligres et al, *Tetrahedron Letters*, (1997), 5253-5256. A solution of the protected aminoester Ih (5.45 g, 15.3 mmol) in dry acetonitrile (250 ml) was treated with K$_2$CO$_3$ (8.95 g, 64.8 mmol) and thiophenol (4.96 ml, 48.6 mmol) and stirred at 50° C. overnight. The mixture was evaporated under vacuum and the residue purified by column chromatography (SiO$_2$, 10:90:1 EtOH:DCM:NH$_4$OH by volume) to afford the title compound as an off-white solid (1.14 g, 59%). $^1$H NMR (400 MHz, DMSO-d$_6$) δ 7.53 (s, 1H), 3.26 (s, 2H), 2.84 (s, 3H), 1.01 (dd, J=6.1, 3.1 Hz, 2H), 0.60 (dd, J=6.1, 3.1 Hz, 2H).

Preparation of 5-(3-Nitro-phenyl)-oxazole (Ia)

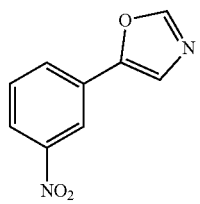

A solution of 3-nitrobenzaldehyde (15.0 g, 99.3 mmol) in methanol (400 ml) was treated with TosMIC (21.3 g, 109 mmol) and $K_2CO_3$ (16.5 g, 119 mmol) and heated to reflux for 30 mins. The cooled solution was concentrated and treated with water (400 ml) to form copious precipitate and was filtered. The filter cake was washed with water, then the solid was taken up in EtOAc and dried over $MgSO_4$. The solution was filtered and evaporated and the resultant solid was dried under vacuum to give the title compound as a beige solid (18.0 g, 95%). $^1$H NMR (400 MHz, DMSO-$d_6$) δ 8.56 (s, 1H), 8.50 (t, J=1.9 Hz, 1H), 8.21 (ddd, J=8.2, 2.3, 1.0 Hz, 1H), 8.17 (ddd, J=7.8, 1.6, 1.0 Hz, 1H), 7.99 (s, 1H), 7.78 (t, J=8.0 Hz, 1H).

Preparation of 3-Oxazol-5-yl-phenylamine (Ib)

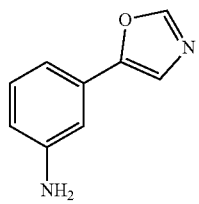 [SMILES: Nc1cccc(-c2cnco2)c1]

A solution of intermediate Ia (3.52 g, 18.5 mmol) in absolute ethanol (210 ml) was treated with water (21 ml) then $SnCl_2.2H_2O$ (20.9 g, 92.6 mmol) and conc. HCl (15 ml, 180 mmol). After stirring at room temperature overnight, the solution was taken to pH 7 with 10% aqueous NaOH solution and extracted repeatedly with EtOAc. The organics were dried ($MgSO_4$), filtered and evaporated to afford the title compound as a pale orange powder (2.74 g, 93%). $^1$H NMR (400 MHz, DMSO-$d_6$) δ 8.37 (s, 1H), 7.49 (s, 1H), 7.10 (t, J=7.8 Hz, 1H), 6.90 (t, J=1.8 Hz, 1H), 6.86 (d, J=7.6 Hz, 1H), 6.59-6.54 (m, 1H), 5.25 (s, 2H).

Preparation of (4-Methyl-pyrimidin-2-yl)-(3-oxazol-5-yl-phenyl)-amine (Ic)

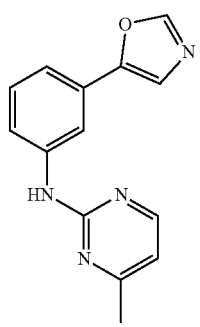 [SMILES: Cc1ccnc(Nc2cccc(-c3cnco3)c2)n1]

A solution of intermediate Ib (1.00 g, 6.24 mmol) in 2-propanol (50 ml) was treated with 2-chloro-4-methylpyrimidine (800 mg, 6.22 mmol) and 1.25M HCl solution in ethanol (7.5 ml, 9.38 mmol) and heated to reflux for 40 h. The solvent was evaporated and the residue made basic with saturated aqueous $NaHCO_3$ and extracted with EtOAc. The organics were dried ($MgSO_4$), filtered and evaporated to afford the title compound as a beige solid (1.04 g, 67%). $^1$H NMR (400 MHz, DMSO-$d_6$) δ 9.71 (s, 1H), 8.45 (s, 1H), 8.37 (d, J=4.9 Hz, 1H), 8.23 (s, 1H), 7.76 (d, J=7.9 Hz, 1H), 7.60 (s, 1H), 7.37 (t, J=7.8 Hz, 1H), 7.30 (d, J=7.5 Hz, 1H), 6.77 (d, J=4.9 Hz, 1H), 2.38 (s, 3H).

Preparation of [3-(2-Chloro-oxazol-5-yl)-phenyl]-(4-methyl-pyrimidin-2-yl)-amine (Id)

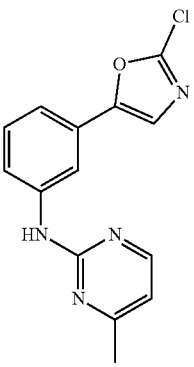 [SMILES: Cc1ccnc(Nc2cccc(-c3cnc(Cl)o3)c2)n1]

A solution of intermediate Ic (1.23 g, 4.88 mmol) in dry THF (60 ml) under argon at −78° C. was treated with 1M LiHMDS solution in THF (7.20 mmol, 7.20 mmol) dropwise. After 45 mins at −78° C., hexachloroethane (1.39 g, 5.87 mmol) was added in one portion and stirring continued for a further 40 mins before warming to RT. The solution was then cooled to −78° C. once more, treated with 1M LiHMDS (7.20 ml, 7.20 mmol) dropwise and immediately allowed to warm to room temperature. The solution was treated with water and extracted with EtOAc. The combined organics were washed with brine, dried ($MgSO_4$), filtered and evaporated. The residue was purified by column chromatography ($SiO_2$, 20% to 30% EtOAc in cyclohexane) to afford the title compound as a pale yellow solid (1.17 g, 84%). $^1$H NMR (400 MHz, DMSO-$d_6$) δ 9.74 (s, 1H), 8.37 (d, J=5.0 Hz, 1H), 8.19 (t, J=1.8 Hz, 1H), 7.79 (dd, J=8.0, 1.8 Hz, 1H), 7.70 (s, 1H), 7.38 (t, J=7.9 Hz, 1H), 7.27 (d, J=7.7 Hz, 1H), 6.78 (d, J=5.0 Hz, 1H), 2.38 (s, 3H).

Preparation of 4-{5-[3-(4-Methyl-pyrimidin-2-ylamino)-phenyl]-oxazol-2-yl}-4,7-diaza-spiro[2.5]octan-8-one (Compound 001)

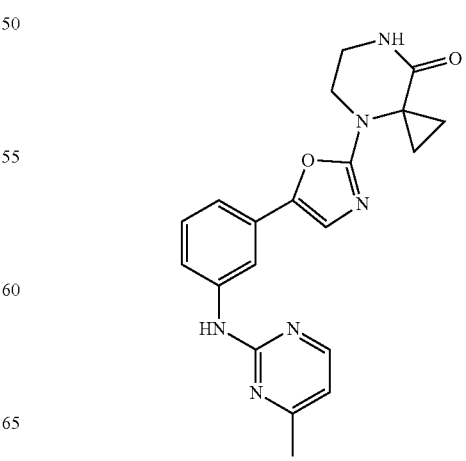

A mixture of intermediate Id (800 mg, 2.79 mmol) and Ie (704 mg, 5.58 mmol) was ground together and heated to 140° C. for 1 h. The cooled solid residue was taken up in a little hot ethanol, treated with NaHCO₃ solution (sat aqu) and extracted with 10% EtOH in DCM. The combined organics were washed with brine, dried (MgSO₄), filtered and evaporated. The residue was purified by column chromatography (SiO₂, 10% EtOH in DCM) to afford the title compound as a beige solid (691 mg, 66%). $^1$H NMR (400 MHz, DMSO-$d_6$) δ 9.63 (s, 1H), 8.35 (d, J=5.0 Hz, 1H), 8.09 (t, J=1.8 Hz, 1H), 7.77 (s, 1H), 7.66 (dd, J=8.1, 1.3 Hz, 1H), 7.31-7.26 (m, 2H), 7.14 (d, J=7.8 Hz, 1H), 6.76 (d, J=5.0 Hz, 1H), 3.85 (t, J=5.7 Hz, 2H), 3.44 (td, J=5.7, 1.5 Hz, 2H), 2.38 (s, 3H), 1.46 (dd, J=7.8, 4.5 Hz, 2H), 1.32 (dd, J=7.7, 4.4 Hz, 2H).

Example 002

Synthetic Approach of Compound 002

Preparation of 2-Chloro-5-(3-nitro-phenyl)-oxazole (IIa)

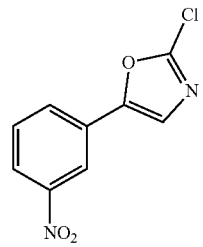 [SMILES: O=[N+]([O-])c1cccc(-c2cnc(Cl)o2)c1]

Prepared as for Intermediate Id above from Intermediate Ia followed by purification by column chromatography (SiO₂, 20% EtOAc in cyclohexane) to afford the title compound as a pale yellow solid (77%). $^1$H NMR (400 MHz, CDCl₃) δ 8.45-8.43 (m, 1H), 8.21 (ddd, J=8.2, 2.2, 0.9 Hz, 1H), 7.91 (ddd, J=7.8, 1.5, 1.0 Hz, 1H), 7.64 (t, J=8.0 Hz, 1H), 7.46 (s, 1H).

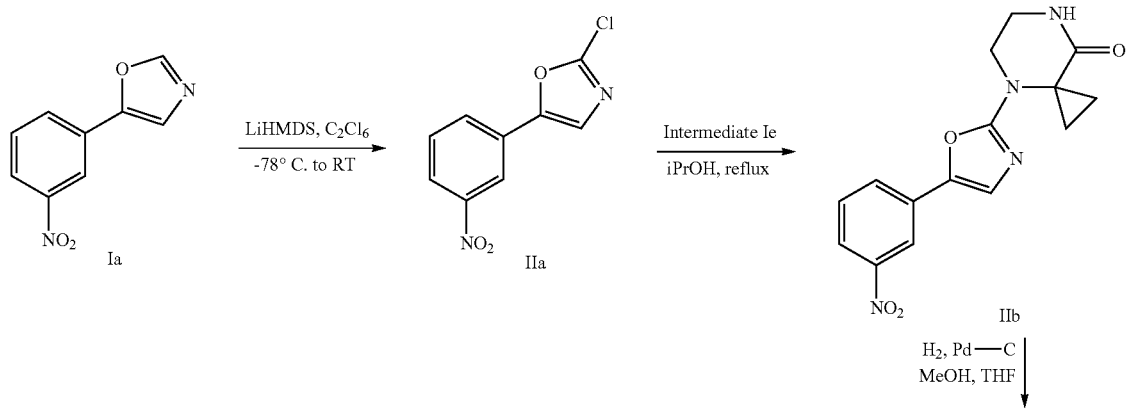

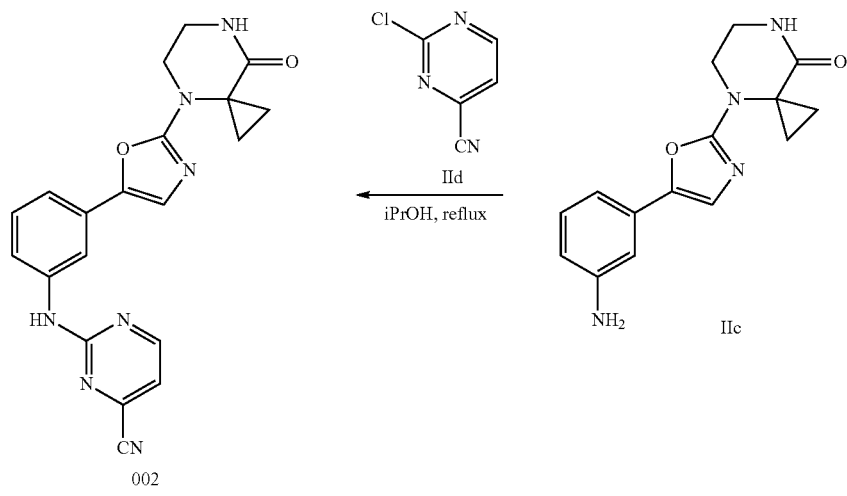

Preparation of 4-[5-(3-Nitro-phenyl)-oxazol-2-yl]-4,7-diaza-spiro[2.5]octan-8-one (IIb)

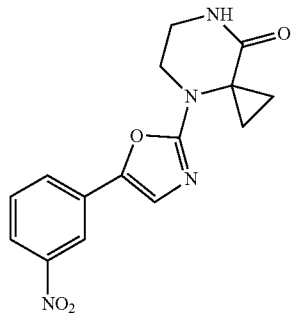

A solution of intermediate IIa (500 mg, 2.23 mmol) and 4,7-diaza-spiro[2.5]octan-8-one Ie (842 mg, 6.68 mmol) in 2-propanol (100 ml) was heated to reflux for 10 days. The mixture was cooled to ambient temperature, concentrated under vacuum and the yellow precipitate formed removed by filtration and dried in a dessicator to give the title compound as a yellow solid (410 mg, 59%). $^1$H NMR (400 MHz, DMSO-$d_6$) δ 8.33 (s, 1H), 8.08 (dd, J=8.1, 1.9 Hz, 1H), 7.99 (d, J=7.9 Hz, 1H), 7.80 (s, 1H), 7.75-7.66 (m, 2H), 3.90 (t, J=5.6 Hz, 2H), 3.42 (t, J=4.6 Hz, 2H), 1.45 (dd, J=7.7, 4.5 Hz, 2H), 1.32 (dd, J=7.7, 4.4 Hz, 2H).

Preparation of 4-[5-(3-Amino-phenyl)-oxazol-2-yl]-4,7-diaza-spiro[2.5]octan-8-one (IIc)

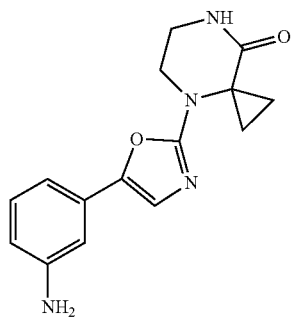 [SMILES: O=C1NCCN(c2ncc(-c3cccc([N+](=O)[O-])c3)o2)C12CC2]

A slurry of the nitrooxazole IIb (360 mg, 1.15 mmol) and 10% Pd/C (50 mg) in THF (60 ml) and methanol (40 ml) was stirred under an atmosphere of hydrogen at ambient temperature and atmospheric pressure for 16 h. The solution was filtered and evaporated under vacuum before purification by column chromatography (SiO$_2$, 5% EtOH in DCM) to afford the title compound as a white solid (230 mg, 79%). $^1$H NMR (400 MHz, DMSO-$d_6$) δ 7.79 (s, 1H), 7.19 (s, 1H), 7.04 (t, J=7.8 Hz, 1H), 6.74-6.69 (m, 2H), 6.46 (dd, J=7.9, 1.9 Hz, 1H), 5.19 (s, 2H), 3.82 (t, J=5.6 Hz, 2H), 3.43-3.38 (m, 2H), 1.43 (dd, J=7.8, 4.5 Hz, 2H), 1.27 (dd, J=7.7, 4.4 Hz, 2H).

Preparation of 2-Chloro-4-cyanopyrimidine (IId)

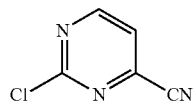

Prepared largely according to the method described in WO2005/075468. A solution of 4-methyl-1H-pyrimidin-2-one hydrochloride (14.7 g, 100 mmol) in 50% aqueous acetic acid (100 ml) at 15° C. was treated with sodium nitrite in one portion (10.4 g, 150 mmol) with vigorous stirring causing an exothermic reaction (40° C.). A yellow precipitate was filtered off, washed with cold water and dried in a vacuum dessicator to afford the 2-hydroxy-pyrimidine-4-carbaldehyde oxime intermediate as a pale yellow solid (13.1 g, 94%) $^1$H NMR (400 MHz, DMSO-$d_6$) δ 12.44 (s, 1H), 11.87 (br s, 1H), 7.92 (d, J=6.3 Hz, 1H), 7.77 (d, J=0.4 Hz, 1H), 6.66 (dd, J=6.4, 0.9 Hz, 1H). The oxime was treated with phosphorus oxychloride (20 ml) and warmed slowly to 45° C. Warming was stopped as the temperature rose suddenly to 70° C. and the mixture stirred for 3 h. Diisopropylethylamine (2 ml) was added and the mixture refluxed for 30 mins before pouring into ice and extraction with DCM. The organics were washed with water then NaHCO$_3$ (sat aqu) then again with water, dried (MgSO$_4$), filtered and evaporated to afford Intermediate IId as a yellow oil which crystallized on standing (1.51 g, 30%). $^1$H NMR (400 MHz, DMSO-$d_6$) δ 9.15 (d, J=4.9 Hz, 1H), 8.25 (d, J=4.9 Hz, 1H).

Preparation of 2-{3-[2-(8-Oxo-4,7-diaza-spiro[2.5]oct-4-yl)-oxazol-5-yl]-phenylamino}-pyrimidine-4-carbonitrile (Compound 002)

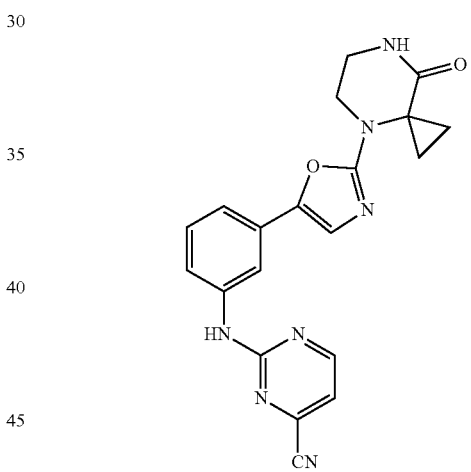

A solution of Intermediate IIc (45 mg, 0.158 mmol) and 2-chloro-4-cyanopyrimidine IId (66 mg, 0.474 mmol) in 2-propanol (3 ml) was heated to reflux for 40 h. The formed precipitate was filtered and treated with NaHCO$_3$ solution (sat aqu) and extracted with 10% EtOH in DCM (50 mL). The combined organics were dried (MgSO$_4$), filtered and then partially concentrated under vacuum. The precipitate was collected by filtration, washed with ether and dried to afford (compound 002 as a yellow solid (39 mg, 64%). $^1$H NMR (400 MHz, DMSO-$d_6$) δ 10.31 (s, 1H), 8.79 (d, J=4.7 Hz, 1H), 7.95 (s, 1H), 7.81 (s, 1H), 7.59 (d, J=8.2 Hz, 1H), 7.41 (d, J=4.8 Hz, 1H), 7.39-7.33 (m, 2H), 7.25 (d, J=7.7 Hz, 1H), 3.85 (t, J=5.6 Hz, 2H), 3.44 (t, J=6.0 Hz, 2H), 1.46 (dd, J=7.8, 4.5 Hz, 2H), 1.32 (dd, J=7.6, 4.4 Hz, 2H).

Non-commercially available 2-chloro-4-alkylpyrimidines intermediates which were used to prepare compounds listed in the Compound Table, were prepared according to the method of Jorgensen et al (*J. Am. Chem. Soc.*, (2011), 15686-15696).

Preparation of 2-Chloro-4-ethylpyrimidine (IIIa)

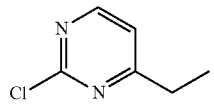

A mixture of 2,4-dichloropyrimidine (2.00 g, 13.4 mmol) and Fe(acac)$_3$ (954 mg, 2.70 mmol) in dry THF (24 ml) at −78° C. under argon was treated with a solution of ethylmagnesium bromide (lm in THF, 16.2 ml, 16.2 mmol) dropwise. After stirring at −78° C. for 30 mins, the mixture was warmed to ambient temperature and stirred for a further hour. The mixture was again cooled to −78° C. and treated with ethylmagnesium bromide solution (10 ml, 10 mmol) and warmed to RT. The mixture was diluted with water, extracted with EtOAc and the organics dried (MgSO$_4$), filtered and evaporated. The residue was purified by column chromatography (SiO$_2$, 20% EtOAc in cyclohexane) to afford the title compound as a clear liquid (642 mg, 34%). $^1$H NMR (400 MHz, DMSO-d$_6$) δ 8.64 (d, J=5.1 Hz, 1H), 7.47 (d, J=5.1 Hz, 1H), 2.76 (q, J=7.6 Hz, 2H), 1.21 (t, J=7.6 Hz, 3H).

The 2-chloro-4-aryl-2-ylpyrimidine and 2-chloro-4-heteroaryl-2-ylpyrimidine intermediates which were used to prepare compounds listed in the Compound Table, were prepared by Suzuki coupling methods (See for example, N. Miyaura and A. Suzuki, *Chemical Reviews* (1995), 2457-2483).

Preparation of 2-Chloro-4-thiophen-2-ylpyrimidine (IIIb)

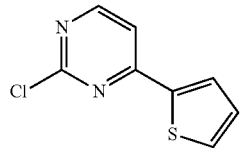 [SMILES: Clc1nccc(-c2cccs2)n1]

A mixture of 2,4-dichloropyrimidine (1.00 g, 6.71 mmol), 2-thiopheneboronic add (430 mg, 3.36 mmol), Na$_2$CO$_3$ (0.4M solution in water, 20 ml, 8.06 mmol) and Pd(PPh$_3$)$_4$ (78 mg, 0.067 mmol) in THF (20 ml) was heated to 90° C. overnight. The cooled mixture was diluted with water, extracted with DCM and the organics dried (MgSO$_4$), filtered and evaporated. The residue was purified by column chromatography (SiO$_2$, 20% EtOAc in cyclohexane) to afford the title compound as a white solid (591 mg, 89%). $^1$H NMR (400 MHz, DMSO-d$_6$) δ 8.73 (d, J=5.3 Hz, 1H), 8.16 (dd, J=3.8, 1.1 Hz, 1H), 8.04 (d, J=5.3 Hz, 1H), 7.95 (dd, J=5.0, 1.1 Hz, 1H), 7.29 (dd, J=5.0, 3.8 Hz, 1H).

4-Amino-2-chloro-pyrimidines intermediates, which were used to prepare compounds listed in the Compound Table, were prepared according to the method below largely based on that described in US2006/199804.

Preparation of 4-(2-Chloro-pyrimidin-4-yl)-morpholine (IIIc)

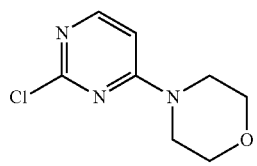 [SMILES: Clc1nccc(N2CCOCC2)n1]

A stirred solution of 2,4-dichloropyrimidine (5.00 g, 36.5 mmol) and diisopropylethylamine (14.0 ml, 80.4 mmol) in EtOH (60 ml) at 0° C. was treated with morpholine (3.18 ml, 36.5 mmol) and allowed to warm to ambient temperature overnight. The solution was poured into brine and extracted with DCM. The organics were dried (MgSO$_4$), filtered and evaporated. The residue was purified by column chromatography (SiO$_2$, 5% EtOH in DCM) to afford the title compound IIIc as a white solid (1.3 g, 36%). $^1$H NMR (300 MHz, DMSO-d$_6$) δ 8.10 (d, J=6.2 Hz, 1H), 6.83 (d, J=6.2 Hz, 1H), 3.72-3.49 (m, 8H).

Preparation of 4-{5-[3-(4-Methyl-pyridin-2-ylamino)-phenyl]-oxazol-2-yl}-4,7-diaza-spiro[2.5]octan-8-one (Compound 021)

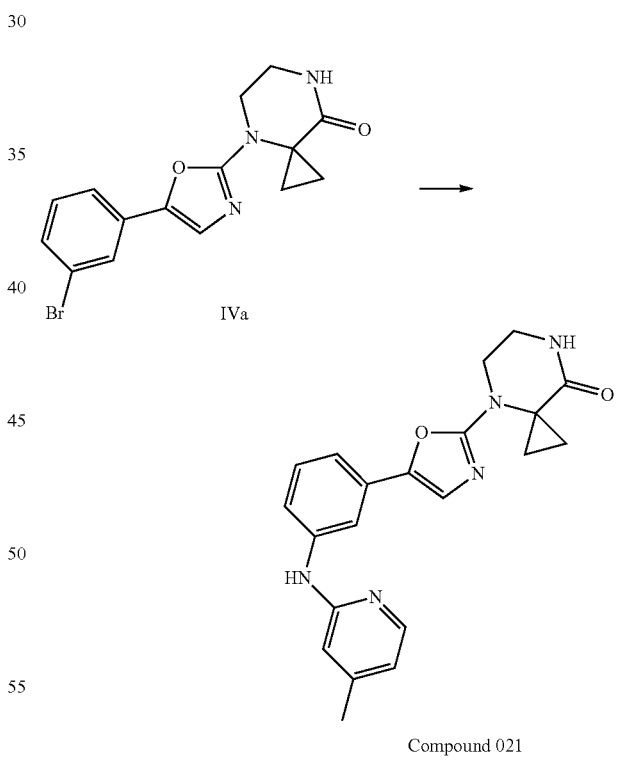

4-[5-(3-Bromo-phenyl)-oxazol-2-yl]-4,7-diaza-spiro[2.5]octan-8-one (IVa) was prepared from 3-bromobenzaldehyde in 3 steps as described for intermediates Ia, IIa and IIb. $^1$H NMR (400 MHz, DMSO-d$_6$) δ 7.81 (s, 1H), 7.77 (t, J=1.7 Hz, 1H), 7.58-7.54 (m, 1H), 7.54 (s, 1H), 7.44 (ddd, J=8.0, 1.7, 1.1 Hz, 1H), 7.37 (t, J=7.9 Hz, 1H), 3.87 (t, J=5.7 Hz, 2H), 3.40 (td, J=5.5, 1.6 Hz, 2H), 1.42 (dd, J=7.8, 4.5 Hz, 2H), 1.29 (dd, J=7.7, 4.4 Hz, 2H).

A solution of Intermediate IVa (100 mg, 0.287 mmol) in degassed dioxane (5 ml) and in a sealed tube was treated with 2-amino-4-methylpyridine (47 mg, 0.431 mmol), Pd$_2$(dba)$_3$ (5 mg, 0.00574 mmol), xantphos (7 mg, 0.0115 mmol) and Cs$_2$CO$_3$ (140 mg, 0.431 mmol). The tube was sealed and heated to 100° C. overnight. After a further addition of Pd$_2$(dba)$_3$ (20 mg, 0.0218 mmol) and xantphos (28 mg, 0.0484 mmol) the mixture was heated for a further 24 h. The cooled mixture was treated with water and extracted with DCM and the organics dried (MgSO$_4$), filtered and evaporated. The residue was purified first by column chromatography (SiO$_2$, 5%-10% EtOH in DCM) then by trituration with EtOAc to afford compound 021 as a cream colored solid (32 mg, 30%). $^1$H NMR (400 MHz, DMSO-d$_6$) δ 9.01 (s, 1H), 8.04 (d, J=5.1 Hz, 1H), 7.95 (s, 1H), 7.79 (s, 1H), 7.54 (dd, J=8.2, 1.2 Hz, 1H), 7.29 (s, J=2.7 Hz, 1H), 7.26 (t, J=8.0 Hz, 1H), 7.08 (d, J=7.7 Hz, 1H), 6.66 (s, 1H), 6.62 (d, J=5.2 Hz, 1H), 3.85 (t, J=5.5 Hz, 2H), 3.44 (t, J=4.4 Hz, 2H), 2.24 (s, 3H), 1.46 (dd, J=7.7, 4.4 Hz, 2H), 1.32 (dd, J=7.6, 4.4 Hz, 2H).

Preparation of 4-{5-[3-(Thiazol-2-ylamino)-phenyl]-oxazol-2-yl}-4,7-diaza-spiro[2.5]octan-8-one (Compound 022)

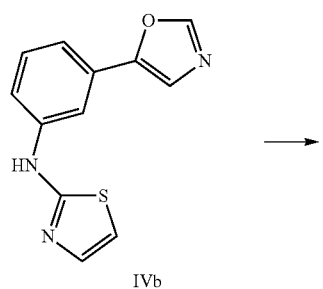

IVb

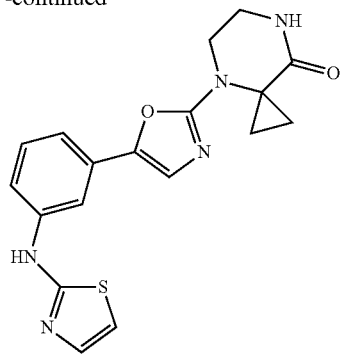

Compound 022

A solution of intermediate Ib (1.50 g, 9.37 mmol) in EtOH (45 ml) and water (5 ml) was treated with 2-bromothiazole (1.69 ml, 18.7 mmol) and conc. HCl (1.61 ml, 187 mmol) and stirred at 100° C. for 6 h. After addition of further 2-bromothiazole (1.69 ml, 18.7 mmol) the solution was heated for a further 24 h then cooled and taken to pH14 with aqueous NaOH solution. After extraction with 10% EtOH in DCM then DCM, the organics were dried (MgSO$_4$), filtered and evaporated. The residue was purified by column chromatography (SiO$_2$, 5% acetone in DCM) to afford intermediate IVb as a white solid (493 mg, 22%). $^1$H NMR (300 MHz, DMSO-d$_6$) δ 10.36 (s, 1H), 8.46 (s, 1H), 8.10 (t, J=1.8 Hz, 1H), 7.63 (s, 1H), 7.56 (ddd, J=8.1, 2.2, 1.1 Hz, 1H), 7.39 (t, J=7.9 Hz, 1H), 7.33-7.29 (m, 2H), 6.95 (d, J=3.7 Hz, 1H).

Compound 022 was then prepared from intermediate IVb as described for intermediate Id and Compound 001 above: $^1$H NMR (300 MHz, DMSO-d$_6$) δ 10.29 (s, 1H), 7.84 (s, 1H), 7.81 (s, 1H), 7.54 (dd, J=8.1, 1.3 Hz, 1H), 7.37-7.29 (m, 2H), 7.27 (d, J=3.6 Hz, 1H), 7.15 (d, J=7.8 Hz, 1H), 6.94 (d, J=3.7 Hz, 1H), 3.85 (t, J=5.5 Hz, 2H), 3.43 (s, 2H), 1.46 (dd, J=7.7, 4.5 Hz, 2H), 1.32 (dd, J=7.6, 4.5 Hz, 2H).

By repeating the methods described above using the appropriate starting materials and conditions, the following additional analogues in the compound Table 1 were prepared and characterized.

Compound Table 1

| Ex # | Chemical structure | Name | Syk (IC50) | LCMS |
|---|---|---|---|---|
| 001 | 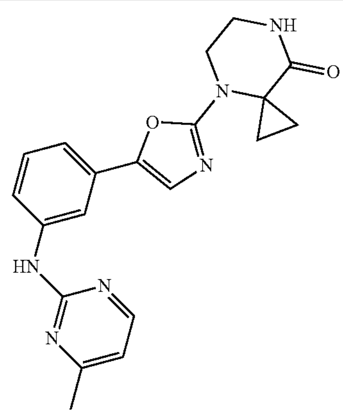 [SMILES: Cc1ccnc(Nc2cccc(-c3cnc(N4CCNC(=O)C45CC5)o3)c2)n1] | 4-{5-[3-(4-Methyl-pyrimidin-2-ylamino)-phenyl]-oxazol-2-yl}-4,7-diaza-spiro[2.5]octan-8-one | +++ | m/z 377.4 (1M + H) tR = 2.42 mins |

Compound Table 1

| Ex # | Chemical structure | Name | Syk (IC50) | LCMS |
|---|---|---|---|---|
| 002 | 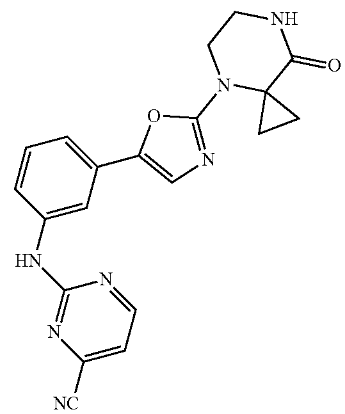 [SMILES: N#Cc1ccnc(Nc2cccc(-c3cnc(N4CCNC(=O)C45CC5)o3)c2)n1] | 2-{3-[2-(8-Oxo-4,7-diaza-spiro[2.5]oct-4-yl)-oxazol-5-yl]-phenylamino}-pyrimidine-4-carbonitrile | +++ | m/z 388.3 (M + H) tR = 2.57 mins |
| 003 | 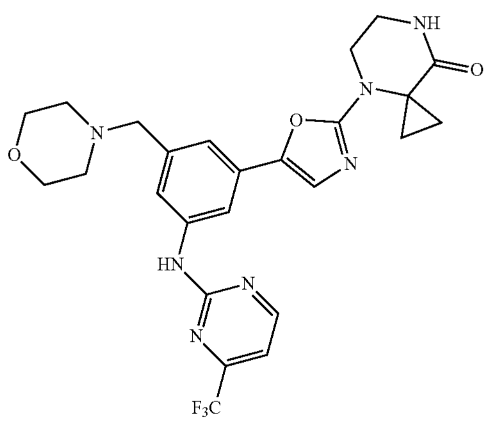 [SMILES: O=C1NCCN(c2ncc(-c3cc(CN4CCOCC4)cc(Nc4nccc(C(F)(F)F)n4)c3)o2)C12CC2] | 4-{5-[3-Morpholin-4-ylmethyl-5-(4-trifluoromethyl-pyrimidin-2-ylamino)-phenyl]-oxazol-2-yl}-4,7-diaza-spiro[2.5]octan-8-one | +++ | m/z 530.5 (M + H) tR = 2.04 mins |
| 004 | 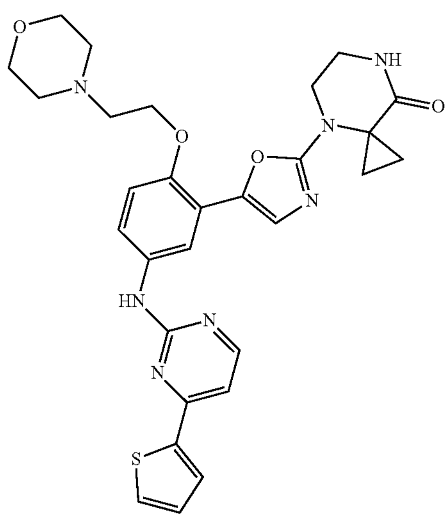 [SMILES: O=C1NCCN(c2ncc(-c3cc(Nc4nccc(-c5cccs5)n4)ccc3OCCN3CCOCC3)o2)C12CC2] | 4-{5-[2-(2-Morpholin-4-yl-ethoxy)-5-(4-thiophen-2-yl-pyrimidin-2-ylamino)-phenyl]-oxazol-2-yl}-4,7-diaza-spiro[2.5]octan-8-one | +++ | m/z 574.5 (M + H) tR = 2.15 mins |

Compound Table 1

| Ex # | Chemical structure | Name | Syk (IC50) | LCMS |
|---|---|---|---|---|
| 005 | 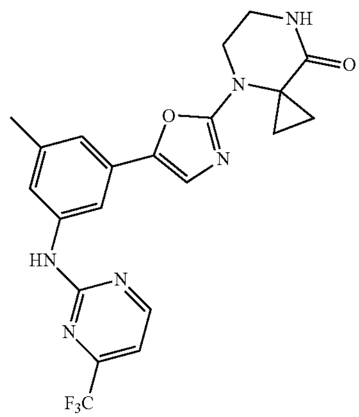 [SMILES: Cc1cc(Nc2nccc(C(F)(F)F)n2)cc(-c2cnc(N3CCNC(=O)C34CC4)o2)c1] | 4-{5-[3-Methyl-5-(4-trifluoromethyl-pyrimidin-2-ylamino)-phenyl]-oxazol-2-yl}-4,7-diaza-spiro[2.5]octan-8-one | +++ | m/z 445.4 (M + H) tR = 3.11 mins |
| 006 | 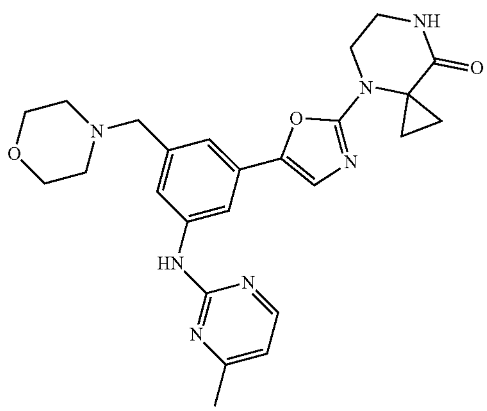 [SMILES: Cc1ccnc(Nc2cc(CN3CCOCC3)cc(-c3cnc(N4CCNC(=O)C45CC5)o3)c2)n1] | 4-{5-[3-(4-Methyl-pyrimidin-2-ylamino)-5-morpholin-4-ylmethyl-phenyl]-oxazol-2-yl}-4,7-diaza-spiro[2.5]octan-8-one | +++ | m/z 476.5 (M + H) tR = 1.78 mins |
| 007 | 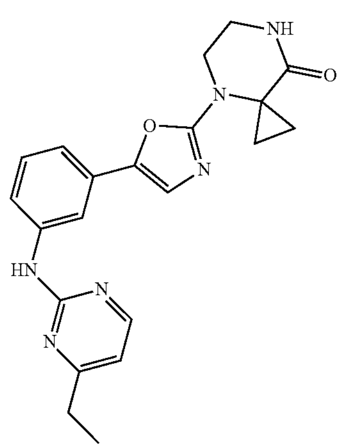 [SMILES: CCc1ccnc(Nc2cccc(-c3cnc(N4CCNC(=O)C45CC5)o3)c2)n1] | 4-{5-[3-(4-Ethyl-pyrimidin-2-ylamino)-phenyl]-oxazol-2-yl}-4,7-diaza-spiro[2.5]octan-8-one | +++ | m/z 391.4 (M + H) tR = 2.68 mins |

-continued

Compound Table 1

| Ex # | Chemical structure | Name | Syk (IC50) | LCMS |
|---|---|---|---|---|
| 008 | 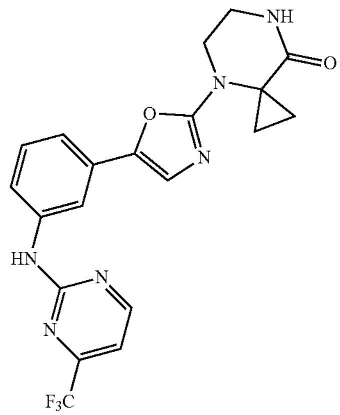 [SMILES: O=C1NCCN(c2ncc(-c3cccc(Nc4nccc(C(F)(F)F)n4)c3)o2)C12CC2] | 4-{5-[3-(4-Trifluoromethyl-pyrimidin-2-ylamino)-phenyl]-oxazol-2-yl}-4,7-diaza-spiro[2.5]octan-8-one | +++ | m/z 431.4 (M + H) tR = 2.95 mins |
| 009 | 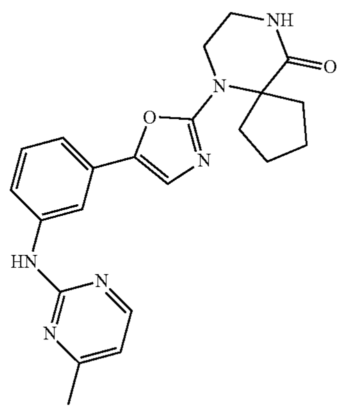 [SMILES: Cc1ccnc(Nc2cccc(-c3cnc(N4CCNC(=O)C45CCCC5)o3)c2)n1] | 6-{5-[3-(4-Methyl-pyrimidin-2-ylamino)-phenyl]-oxazol-2-yl}-6,9-diaza-spiro[4.5]decan-10-one | +++ | m/z 405.5 (M + H) tR = 2.70 mins |
| 010 | 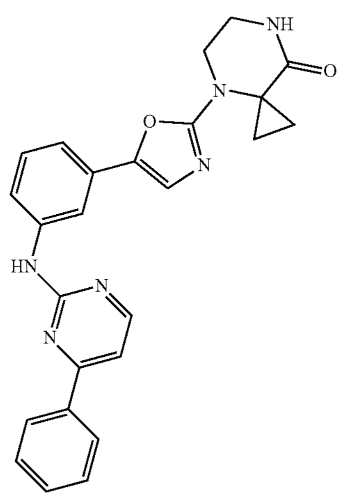 [SMILES: O=C1NCCN(c2ncc(-c3cccc(Nc4nccc(-c5ccccc5)n4)c3)o2)C12CC2] | 4-{5-[3-(4-Phenyl-pyrimidin-2-ylamino)-phenyl]-oxazol-2-yl}-4,7-diaza-spiro[2.5]octan-8-one | +++ | m/z 439.4 (M + H) tR = 3.10 mins |

Compound Table 1

| Ex # | Chemical structure | Name | Syk (IC50) | LCMS |
|------|--------------------|------|------------|------|
| 011 | 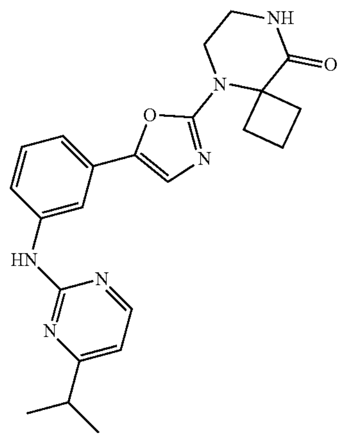 [SMILES: CC(C)c1ccnc(Nc2cccc(-c3cnc(N4CCNC(=O)C45CCC5)o3)c2)n1] | 5-{5-[3-(4-Isopropyl-pyrimidin-2-ylamino)-phenyl]-oxazol-2-yl}-5,8-diaza-spiro[3.5]non-9-one | +++ | m/z 419.5 (M + H) tR = 3.14 mins |
| 012 | 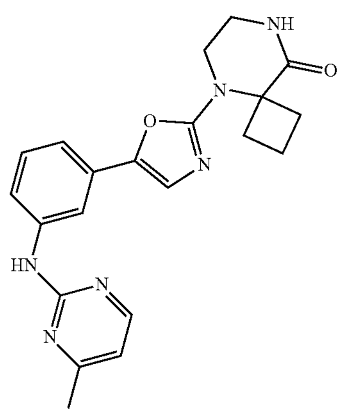 [SMILES: Cc1ccnc(Nc2cccc(-c3cnc(N4CCNC(=O)C45CCC5)o3)c2)n1] | 5-{5-[3-(4-Methyl-pyrimidin-2-ylamino)-phenyl]-oxazol-2-yl}-5,8-diaza-spiro[3.5]nonan-9-one | +++ | m/z 391.4 (M + H) tR = 2.60 mins |
| 013 | 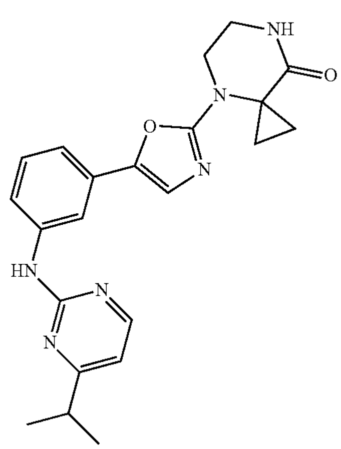 [SMILES: CC(C)c1ccnc(Nc2cccc(-c3cnc(N4CCNC(=O)C45CC5)o3)c2)n1] | 4-{5-[3-(4-Isopropyl-pyrimidin-2-ylamino)-phenyl]-oxazol-2-yl}-4,7-diaza-spiro[2.5]octan-8-one | +++ | m/z 405.4 (M + H) tR = 2.93 mins |

-continued
Compound Table 1
| Ex # | Chemical structure | Name | Syk (IC50) | LCMS |
|---|---|---|---|---|
| 014 | 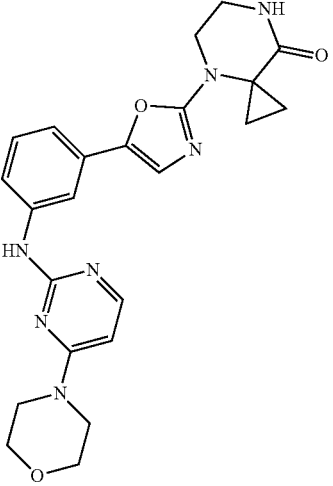 [SMILES: O=C1NCCN(c2ncc(-c3cccc(Nc4nccc(N5CCOCC5)n4)c3)o2)C12CC2] | 4-{5-[3-(4-Morpholin-4-yl-pyrimidin-2-ylamino)-phenyl]-oxazol-2-yl}-4,7-diaza-spiro[2.5]octan-8-one | + | m/z 448.5 (M + H) tR = 1.85 mins |
| 015 | 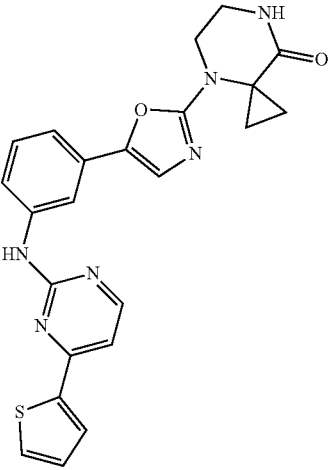 [SMILES: O=C1NCCN(c2ncc(-c3cccc(Nc4nccc(-c5cccs5)n4)c3)o2)C12CC2] | 4-{5-[3-(4-Thiophen-2-yl-pyrimidin-2-ylamino)-phenyl]-oxazol-2-yl}-4,7-diaza-spiro[2.5]octan-8-one | +++ | m/z 445.4 (M + H) tR = 2.95 mins |
| 016 | 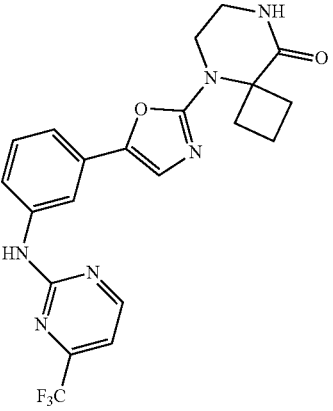 [SMILES: O=C1NCCN(c2ncc(-c3cccc(Nc4nccc(C(F)(F)F)n4)c3)o2)C12CCC2] | 5-{5-[3-(4-Trifluoromethyl-pyrimidin-2-ylamino)-phenyl]-oxazol-2-yl}-5,8-diaza-spiro[3.5]nonan-9-one | +++ | m/z 445.4 (M + H) tR = 3.14 mins |

Compound Table 1
| Ex # | Chemical structure | Name | Syk (IC50) | LCMS |
|---|---|---|---|---|
| 017 | 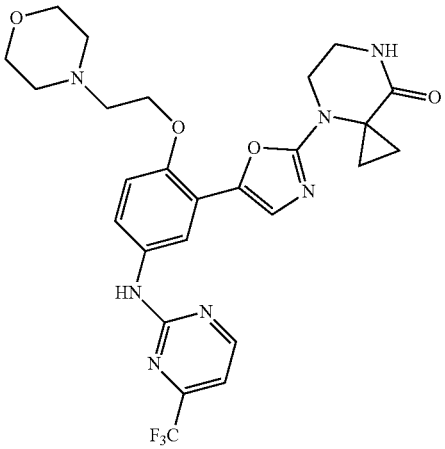 [SMILES: O=C1NCCN(c2ncc(-c3cc(Nc4nccc(C(F)(F)F)n4)ccc3OCCN3CCOCC3)o2)C12CC2] | 4-{5-[2-(2-Morpholin-4-yl-ethoxy)-5-(4-trifluoromethyl-pyrimidin-2-ylamino)-phenyl]-oxazol-2-yl}-4,7-diaza-spiro[2.5]octan-8-one | +++ | m/z 560.6 (M + H) tR = 2.16 mins |
| 018 | 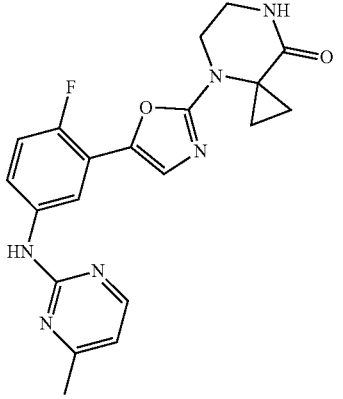 [SMILES: Cc1ccnc(Nc2ccc(F)c(-c3cnc(N4CCNC(=O)C45CC5)o3)c2)n1] | 4-{5-[2-Fluoro-5-(4-methyl-pyrimidin-2-ylamino)-phenyl]-oxazol-2-yl}-4,7-diaza-spiro[2.5]octan-8-one | +++ | m/z 395.4 (M + H) tR = 2.55 mins |
| 019 | 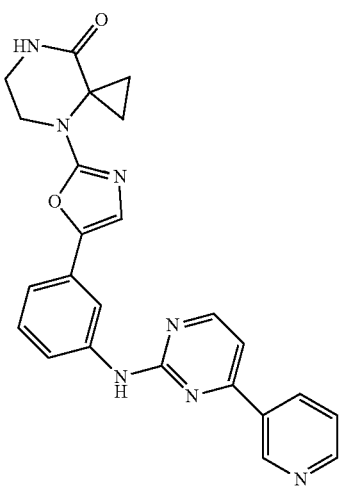 | 4-{5-[3-(4-Pyridin-3-yl-pyrimidin-2-ylamino)-phenyl]-oxazol-2-yl}-4,7-diaza-spiro[2.5]octan-8-one | +++ | m/z 440.2 (M + H) tR = 2.28 mins |

-continued

Compound Table 1

| Ex # | Chemical structure | Name | Syk (IC50) | LCMS |
|---|---|---|---|---|
| 020 | 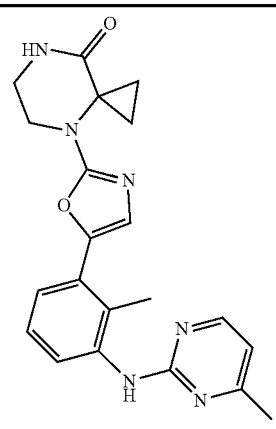 | 4-{5-[2-Methyl-3-(4-methyl-pyrimidin-2-ylamino)-pheny]-oxazol-2-yl}-4,7-diaza-spiro[2.5]octan-8-one | + | m/z 391.2 (M + H) tR = 2.19 mins |
| 021 | 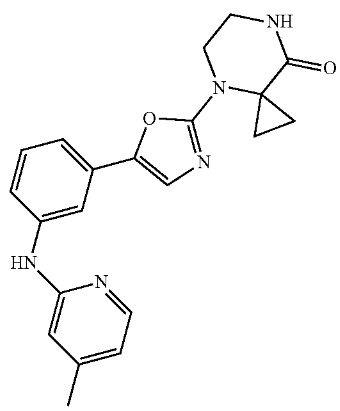 [SMILES: Cc1ccnc(Nc2cccc(-c3cnc(N4CCNC(=O)C45CC5)o3)c2)c1] | 4-{5-[3-(4-Methyl-pyridin-2-ylamino)-phenyl]oxazol-2-yl}-4,7-diaza-spiro[2.5]octan-8-one | ++ | m/z 376 (M + H) tR = 2.02 mins |
| 022 | 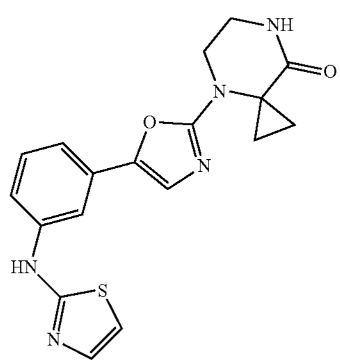 [SMILES: O=C1NCCN(c2ncc(-c3cccc(Nc4nccs4)c3)o2)C12CC2] | 4-{5-[3-(Thiazol-2-ylamino)-phenyl]oxazol-2-yl}-4,7-diaza-spiro[2.5]octan-8-one | +++ | m/z 368 (M + H) tR = 2.67 mins |

IC50: Concentration inhibiting 50% of protein kinase.
The Syk activities given in the Compound Table above are expressed as:
+++: IC50<500 nM
++: 500>IC50<2000 nM
+: IC50>2000 nM

PHARMACOLOGICAL EXAMPLES

1) In Vitro SYK Inhibition Assays
Protocol Inhibition Assays

SYK kinase was purified as a full length protein in a baculovirus system near homogeneity. All kinase assays were performed with the Kinase TK (tyrosine kinase) HTRF (Homogeneous Time Resolved Fluorescence) assay developed by Cisbio international. These assays were carried out at room temperature in 96-wells half-area white plates in a final volume of 25 μl of kinase buffer (10 mM MgCl$_2$; 2 mM MnCl$_2$; 50 mM Sodium-HEPES pH 7.8; BRIJ-35 0.01%, 1 μM substrate) containing ATP at a concentration of at least twice the Km for each enzyme and an appropriate amount of recombinant enzyme to ensure a linear reaction rate. Reactions were initiated upon introduction of the enzyme and terminated with the addition of one reaction volume (25 μl) of HTRF detection buffer. Plates were incubated for one hour at room temperature and the time resolved Fluorescence resonance energy transfer signal was measured in a Pherastar FS microplate reader (BMG Labtech). All data were the average of triplicate results with a standard deviation <10%.

Experimental Results

The experimental results for various compounds according to the invention using above-described protocols are set forth at the compound Table 1.

Comments on the Experiments and Results

The inventors observed a very effective inhibition of SYK by the class of compounds of formula (I) as presently disclosed. The listed compounds in the Compound Table are well representing the class of compounds of formula (I).

The below references to compound 001 referred to the compound of the same number in the Compound Table 1 above. Compound 001 is compared to R406, the active metabolite of fostamatinib/R788, a Rigel Pharmaceutical SYK inhibitor (WO2006/078846A1; Drugs Future, (2011), 36(4): 273-280).

2) In Vitro Anti-SYK Kinase Activity and Selectivity

Activity and selectivity towards SYK target were determined by screening test compounds against various tyrosine kinases using both in vitro recombinant kinase assays and cell-based proliferation assays.

Protocol Inhibition Assays

Cell-based proliferation and viability assay CellTiter-Bleue cell-based survival/proliferation assay (Promega G8080) was performed on BaF3 models.

A total of $1.10^4$ cells/well/50 µl were seeded in a 96-wells plate. Treatment was initiated by addition of a 2× drug solution of ½ serial dilutions ranging from 0 to 10 µM. Cells were grown for 48-72 h at 37° C. and then incubated with 10 µl/well of Promega CellTiter-Bleue reagent for 4 h at 37° C. The amount of formazan dye formed was quantified by its absorbance at 450 nm using a scanning multiwell spectrophotometer (POLARstar Omega, BMG labtech, France). A blank well without cells was used as a background control for the spectrophotometer and all assays were performed in duplicates and the experiments were repeated at least twice.

In Vitro Kinase Assays with Recombinant SYK and Various Protein Kinases

Cloning and Expression of Kinases

Most of the kinases tested in this study were cloned, expressed and purified in the facilities of the inventors. They were expressed either as N-terminus hexahistidine-, hexahistidine-asparagine- or GST-tagged enzymes in a baculovirus or in a Colibacille expression system. Remaining enzymes (JAKs) were purchased from Millipore or Proqinase. For each enzyme, steady state kinetic parameters were determined and validated with known inhibitors. All experiments were performed in a large excess of substrate and with an ATP concentration corresponding at least to 2*Km with respect to ATP.

HTRF Kinase Assay

The analysis of the effect of compounds on kinase activity was assessed with the HTRF® KinEASE assay (Cisbio International), an immuno-assay based on the quantification of the level of phosphorylation of a biotinylated peptide substrate using anti-phospho-specific antibody labeled with Europium ($Eu^{3+}$) cryptate. This assay comprises two steps: —an enzymatic step, during which the peptide substrate, the kinase, ATP, $Mg^{2+}$ and/or $Mn^{2+}$ are incubated with varying concentration of drug (from 0 to 10 µM); —a detection step, at the end of the reaction (stopped by addition of EDTA which chelates $Mg^{2+}$), the antibody anti-phospho peptide-$Eu^{3+}$ (emission 620 nm) and streptavidin XL-665 (emission 665 nm) are added to the reaction mix. After incubation, the obtained signal is proportional to the concentration of phosphorylated peptide in the sample. All measurements were performed on a BMG Labtech Pherastar FS apparatus. Results are expressed in delta fluorescence (DF) unit defined as follow DF %=[(ratio−ratio blank)/(ratio blank)]*100, where ratio=(665 nm/620 nm)*$10^4$. Each experiment was performed in duplicate and repeated two or three times.

Experimental Results

TABLE 2

Activity and selectivity of anti-SYK compounds ($IC_{50}$ µM)

| Protein kinases | Compound 001 | R406 |
| --- | --- | --- |
| TEL-SYK | 0.27 | 1 |
| Jak1* | 3.4 | 0.01 |
| Jak2* | 0.9 | 0.006 |
| Jak3* | 20 | 2.5 |
| Class III receptor tyrosine kinases | | |
| KIT wild-type | 10 | 0.5 |
| KIT D816V | 10 | 0.1 |
| PDGFRβ | — | 0.15 |
| PDGFRα | — | 0.1 |
| Flt3 | 6 | 0.1 |
| c-fms* | — | 5 |
| Other receptor tyrosine kinases | | |
| VEGFR1* | 7.5 | 0.35 |
| VEGFR2* | 20 | 0.06 |
| VEGFR3* | — | <1 |
| EGFR WT/del | — | 3/1 |
| ERBB2 | — | 3 |
| FGFR 1 | — | 0.25 |
| FGFR 3 | — | 0.15 |
| c-Met* | 10 | 20 |
| TrkB | — | 2 |
| IGFR1 | — | 0.9 |
| c-Ret WT/mut* | 10/— | 0.5/0.5 |
| Non receptor tyrosine kinases | | |
| BCR-ABL | 10 | 5 |
| FAK* | — | 0.4 |
| Src* | 2.6 | 0.1 |
| Lyn B* | — | 1 |
| Fyn* | — | 0.05 |
| Lck* | — | — |
| Hck* | — | 15 |
| Btk* | 20 | 0.1 |
| Bmx* | — | 0.12 |
| Fes* | — | 5 |

*enzymatic determination of kinase inhibitory activity of test compounds (otherwise cell-based assay), R406 is the active metabolite of R788/fostamatinib Comments on the Experiments and Results The above in vitro data demonstrated good anti-SYK activity of compound 001. This compound was found more potent than R406 on Ba/F3 TEL-SYK model and exhibited very good selectivity in both cell-based and kinase assays in contrast to the multi-kinase inhibitor R406.

3) In Vitro Anti-SYK Activity in Murine Bone Marrow Mast Degranulation Assay

Protocol Inhibition Assays

In vitro mast cell degranulation assay monitored by released of β-hexosaminidase. Murine bone marrow mast cells (BMMCs) are obtained by flushing bone marrow cells from the femurs of C57BL/6J mice, then cultured for 3-4 weeks in RPMI containing mouse recombinant IL-3 (30 ng/ml). RBL-2H3 is a rat basophile cell line maintained in monolayer culture in EMEM supplemented with 20% FCS, 1 mM Glutamine and 1× antibiotics. Cells were sensitized overnight with 0.2 µg/ml anti-DNP-IgE (Sigma-Aldrich D8406). Cells were washed extensively in Tyrode buffer (10 mM Hepes, 130 mM NaCl, 6.2 mM D-Glucose, 3 mM KCl, 1.4 mM $CaCl_2$, 1 mM $MgCl_2$ and 0.1% BSA. Cells ($5.10^4$ cells/well/90 µl) were plated in triplicates in 96 wells plates. Treatment with SYK kinase inhibitors was initiated by adding 10 µl of 10× concentrated dilutions to obtain 0.01, 0.1, 1 and 10 µM final concentrations. After 2 hours drug treatment, cells were stimulated for 90 min with 125 ng/ml DNP-HAS (Sigma-Aldrich A6661) in a final volume of 110 µl. For measurement of β-hexosaminidase activity, 50 µl of supernatant were collected and incubated with 50 µl of 3.7 mM p-nitrophenol-N-acetyl-β-D-glucosaminidine (PNAG, Sigma-Aldrich N9376) prepared in citrate buffer (pH 4.5). After incubation 90 min at 37° C., the reaction was quenched by addition of 100 µl of sodium carbonate buffer (0.1M $Na_2CO_3$/$NaHCO_3$ pH 10.0). β-hexosaminidase activity was quantified by reading plate absorbance at 405 nm with reference at 620 nm using a PolarSTAR reader plate (BMG labech).

Experimental Results

The activity of anti-SYK compounds was tested in an IgE-mediated mast cell degranulation assay. SYK has been identified to be critical for the initiation of mast cell mediator release following the aggregation of FcεRI. Anti-SYK compound 001 and R406 were compared in their ability to block IgE-mediated release of the granule component β-hexosaminidase. The results are expressed as % of β-hexosaminidase residual activity compared to untreated cells (100%) as shown in Table 3 below.

TABLE 3

Effect of anti-SYK on β-hexosaminidase release/activity

| Drug | β-hexosaminidase activity (% control untreated cells) | | | Kinase activity profile $IC_{50}$ (nM) | | | | |
|---|---|---|---|---|---|---|---|---|
| | 0.01 µM | 0.1 µM | 1 µM | Btk | Syk | Tel-Syk* | Src | JAK 2 |
| R406 | 78 ± 11 (n = 11) | 16 ± 6 (n = 14) | 3 ± 3 (n = 14) | 95 | 34 | 1000 | 100 | 6 |
| Compound 001 | 88 ± 14 (n = 9) | 32 ± 9 (n = 11) | 3 ± 5 (n = 11) | 20000 | 41 | 272 | 2600 | 920 |

*Cell-based assay of test compounds (otherwise enzymatic determination of kinase inhibitory activity).

Comments on the Experiments and Results

Compound 001 was efficient at inhibiting mast cell degranulation ($IC_{50}$=50 nM) in agreement with in vitro kinase assay on purified SYK and cell-based proliferation assay on Ba/F3 tel-SYK cell line. In these experiments, the SYK inhibitor compound 001 was equally potent as the multi-kinase inhibitor R406, at inhibiting mast cell degranulation.

4) In Vitro Anti-SYK Activity in Murine Bone Marrow Mast Cytokine Production
Protocol Inhibition Assays Murine bone marrow mast cells (BMMCs) are obtained by flushing bone marrow cells from the femurs of C57BL/6J mice, and then cultured for 3-4 weeks in RPMI containing mouse recombinant IL-3 (30 ng/ml). Cells were sensitized overnight in IL3-depleted culture medium with 0.1-0.2 µg/ml anti-DNP-IgE (Sigma-Aldrich D8406). Cells were preincubated with inhibitors for 30 min, and then stimulated with 10 ng/ml antigen (Ag) and/or Stem Cell Factor (SCF) (30 ng/ml). The cells were incubated for 6 h. The supernatants were harvested, and the cytokine content measured using CISBIO IL6 and TNFα HTRF assay (cat#63ADKEBU043 and 6FMTNPEB respectively).

Experimental Results

To explore the effect of compound 001 on cytokine production, the production of IL-6 and TNFα in murine bone marrow mast cells (BMMCs) were examined (Table 4 and Table 5).

TABLE 4

FcεRI and Kit-induced TNFα cytokine release in BMMCs.

| | | TNFα Cytokine Release (Relative Fluorescence Units) (% relative to control Ag + SCF) |
|---|---|---|
| Controls | Ag* | −22 |
| | SCF** | 29 |
| | Ag + SCF | 491 (100%) |
| Compound 001 | Ag + SCF + 0.01 µM of compound | 468 (95%) |
| | Ag + SCF + 0.1 µM of compound | 158 (32%) |
| | Ag + SCF + 1 µM of compound | 9.5 (2%) |
| R406 | Ag + SCF + 0.01 µM of compound | 568.5 (120%) |
| | Ag + SCF + 0.1 µM of compound | 171 (35%) |
| | Ag + SCF + 1 µM of compound | −29 (0%) |

*Ag = antigen;
**SCF = Stem Cell Factor

TABLE 5

FcεRI and Kit-induced IL6 cytokine release in BMMCs

| | | IL6 Cytokine Release (Relative Fluorescence Units) ) (% relative to control Ag + SCF) |
|---|---|---|
| Controls | Ag* | −10 |
| | SCF** | 123 |
| | Ag + SCF | 849 (100%) |
| Compound 001 | Ag + SCF + 0.01 µM of compound | 756.5 (89%) |
| | Ag + SCF + 0.1 µM of compound | 249 (29%) |
| | Ag + SCF + 1 µM of compound | 54 (6%) |
| R406 | Ag + SCF + 0.01 µM of compound | 830 (98%) |
| | Ag + SCF + 0.1 µM of compound | 137 (16%) |
| | Ag + SCF + 1 µM of compound | 5 (1%) |

*Ag = antigen;
**SCF = Stem Cell Factor

Comments on the Experiments and Results

As previously reported, IgE-stimulated FcεRI aggregation in the absence of SCF minimally induced cytokine production in BMMCs. However, in the presence of SCF, there was a marked increase in the production and release of IL-6 and TNFα. The release of these cytokines was efficiently blocked by compound 001 ($IC_{50}$~50 nM). In these experiments compound 001 was equally potent as R406 at blocking cytokine release with inhibitory effect observed at concentrations as low as 0.1 µM.

5) In Vivo Anti-SYK Activity in Mouse Model of Asthma
Protocol Assays

Balb/c male mice, 8 weeks old, were purchased from Janvier (Le Genest-Saint-Isle; FRANCE) and bred in the animal facility for 4 weeks. Drugs were dissolved in drinking solvent (80% water; 10% Tween 80 and 10% isopropanediol). It was aliquoted and stored at −20° C. Each mouse received drugs twice a day. The weight of animals was calculated before and after treatment.

Sensitization and Treatment

Mice, 9 weeks of age, were sensitized with 50 µg of ovalbumin (Sigma-Aldrich, Germany) adsorbed to 2 mg Al(OH)$_3$ (Prolabo, France) and diluted in physiological saline (0.9% NaCl). Ovalbumin was injected intraperitoneally on days 1 and 7. Sensitization was followed by intranasal challenges with 10 µg of ovalbumin diluted in 0.9% NaCl, each day from day 18 to day 21. On days 17 to 21, animals treated with drugs received 100 µl of a solution at 15 mg/ml, at 7.5 mg/ml or at 3.75 mg/ml administered per os twice a day during 5 days. These treatments corresponded to concentration of 60 mg/mouse kg, 30 mg/mouse kg and 15 mg/mouse kg respectively.

Assessment of Airway Responsiveness and Lung Function

The airway responsiveness was measured using the invasiveness FlexiVent® (SCIREQ) technique. Briefly, mice were weighed and anesthetized by i.p. with 6 mg/kg of the xylasine solution (Bayer, France) and after 10 minutes with 6 mg/kg of the pentobarbital solution (CEVA). Each anesthetic was diluted in physiological saline solution. Once the mouse was deeply anesthetized, the trachea was canulated and connected to the computer-controlled small animal ventilator (FlexiVent®). When connected, the computer controls the mechanical ventilation with a variety of volume and pressure controlled maneuvers to obtain accurate, reproducible measurement of respiratory mechanics as airway resistance, elastance and compliance. The baseline values were measured after saline solution nebulization and airway hyperresponsiveness evaluated after nebulization of a 0.26M metacholine solution (50 mg/ml).

Assessment of Airway Inflammation

Bronchio-alveolar lavage (BAL) was performed after the animals were disconnected from the FlexiVent®. The airways were lavaged with 5 ml (10 times 0.5 ml) ice cold 0.9% NaCl 2.6 mM EDTA. BAL samples were centrifuged at 1200 rpm for 5 minutes at 4° C. Pellet cells were collected and erythrocytes lysed by adding 1.5 ml deionized water for 30 seconds. After neutralization with 0.5 ml of 0.6M KCl, cells were centrifuged at 1200 rpm for 5 minutes at 4° C. BAL samples were used to count the total cell number and to perform cytospins (shandon, Pontoise). Cell types were identified by morphological criteria after Hemacolor (Merck) staining.

Experimental Results

Compound 001 was evaluated for its impact on airway inflammation and responsiveness in a murine model of asthma, in comparison to Syk inhibitor R406 and the anti-Kit inhibitor Masitinib, an AB Science drug candidate for treating asthma (Allergy, (2009), 64(8):1194-201). Mice were sensitized and challenged with ovalbumin as described in protocol assays above. The mice were distributed in groups of 5-6 animals that were treated twice daily with 7.5 to 60 mg/Kg of anti-SYK/KIT drugs (PO). A summary of the data obtained in several experiments is presented in Table 6.

TABLE 6

Comparison of compound 001 activity with Masitinib and R406 in murine model of asthma

| Compounds | Dose (mg/kg/day) PO | Percentage of Eosinophils recruitment in Bronchio-alveolar lavage (BAL) | Statistical Analysis |
|---|---|---|---|
| Experiment #1 | | | |
| Masitinib | 2 × 7.5 | −15% | $p > 0.05$ |
|  | 2 × 25 | −35% | $p < 0.05$ |
|  | 2 × 30 | −56% | $p < 0.05$ |
| R406 | 2 × 30 | −31% | $p > 0.05$ |
| Experiment #2 | | | |
| Masitinib (n = 12) | 2 × 30 | −47% | $p < 0.05$ |
| Compound 001 (n = 12) | 2 × 15 | −14% | $p > 0.05$ |
|  | 2 × 30 | −47% | $p < 0.05$ |

Comments on the Experiments and Results

Sensitization and challenges with ovalbumin induced a marked increase in the total number of cells, mainly macrophages and eosinophils. Results showed that compound 001 induced a significant decrease of eosinophils recruitment in a dose-dependent manner. C-kit inhibitor Masitinib and compound 001 induced a significant and similar decrease in the number of eosinophils in BAL from sensitized mice at the dose of 30 mg/kg (Table 6, experiment #2), while Masitinib was more potent than R406 in this model of asthma (Table 6, experiment #1). Indeed with a lower dose of Masitinib or compound 001, the same effect as R406 was obtained (Error! Reference source not found.6, experiment #1 and #2). In accordance with airway inflammation analysis, compound 001 treatment reduced bronchial hyper-responsiveness in a dose-dependent manner.

6) In Vivo Anti-SYK Activity in Mouse Model of Rheumatoid Arthritis
Protocol Assays K/B×N serum pools were prepared from arthritic mice at 8 weeks of age. The mice were pre-treated with SYK inhibitors by two per os administration for two days before induction of arthritis. Arthritis was induced in the C57Bl/6 mice (8 weeks of age) by intraperitoneal injection (7.5 µl serum per g weight) at days 0 and 2.

The treatment with SYK inhibitors was continued for 13 days. The control mice were injected with solvent before the induction of arthritis and during the course of the disease. The compounds were dissolved in a solution containing 10% of Tween 80 and 10% 1-2 propandiol. It was prepared before administration.

Ankle thickening measure, being defined as the difference in ankle thickness from the day 0, was measured using a precision calliper. Arthritis/clinical score was defined by sum of scores of each lim (0 no disease; 1 mild swelling of paw or of just of few digits; 2 clear joint inflammation; 3 severe joint inflammation) maximum score=12.

Myeloperoxidase Activity

Myeloperoxidase (MPO) is the most abundant enzyme in primary neutrophils and has been shown to be a useful reliable marker for neutrophil infiltration in inflammatory diseases. MPO activity was determined following published protocol (American Journal of Pathology, (2000), 156 (6): 2169-2177). Briefly, tissue samples were weighed and suspended in 50 mmol/L potassium phosphate buffer (pH 6.0) containing 5 mg/ml hexadecyltrimethylammonium bromide (Sigma Chemical Co.) at a ratio of 50 mg tissue to 1 ml of buffer. Tissues were homogenized by a polytron tissue homogenizer for 1 min, and 1 ml was decanted into sterile Eppendorf tubes and centrifuged at 12,000 rpm for 15 minutes. Using a microtiter plate scanner, 200 µl of the reaction mixture (containing 16.7 mg of o-dianisidine (Sigma Chemical Co.), 90 µl of distilled $H_2O$, 10 µl of potassium-phosphate buffer, and 50 µl of 1% $H_2O_2$) was added to each well containing 7 µl of sample in a standard 96-well plate and three absorbance readings at 5 min intervals at 450 nm were recorded.

Experimental Results

K/BxN was a murine model of spontaneous rheumatoid arthritis that mimics many of the clinical and histological features of human disease with synovitis predominantly in the distal small joints. Arthritis was induced by intraperitoneal injection of arthritis serum of K/BxN mice at days 0 and 2 as described in protocol assays above. Compound 001 was tested at 15 and 50 mg/kg/day b.i.d. and compared with Masitinib at 50 mg/kg/day b.i.d., an AB Science drug candidate for treating rheumatoid arthritis (Arthritis Res Ther., (2009), 11(3):R95). Ankle thickening and arthritis score were used to monitor the in vivo activity of the compounds. Data showed that compound 001 significantly improves the arthritis symptoms in a dose-dependent manner (Table 7).

TABLE 7

Comparison of compound 001 and Masitinib in murine model of arthritis

| Compounds | Ankle Thickening Score | Arthritis Score |
|---|---|---|
| Masitinib 50 mg/kg b.i.d. | −27% P < 0.05 | −15% |
| Compound 001, 15 mg/kg b.i.d. | −17% | −23% |
| Compound 001, 50 mg/kg b.i.d. | −52% P < 0.005 | −68% P < 0.005 |

Myeloperoxidase (MPO) is the most abundant enzyme in primary neutrophils and has been shown to be a useful reliable marker for neutrophil infiltration in inflammatory diseases. MPO activity has been measured with different doses of compound 001 (Table 8).

TABLE 8

MPO dosage following treatment with compound 001

| | Control | KBxN | KBxN + 15 mg/kg Compound 001 b.i.d. | KBxN + 50 mg/kg Compound 001 b.i.d. |
|---|---|---|---|---|
| MPO activity (U/ml) | 0.118 ± 0.01 | 1.104 ± 0.27 | 1.031 ± 0.24 | 0.348 ± 0.08 (p < 0.05) |

Comments on the Experiments and Results

The results of Table 7 has shown that compound 001 administered at 2×50 mg/kg/day was very efficient at decreasing arthritis score with 52 and 68% reduction of ankle thickening and arthritis score respectively with a dose-dependent effect Compound 001 was dearly and significantly more potent in this model of rheumatoid arthritis when compared with Masitinib at the same dosage.

An increase in MPO activity (U/ml) was measured in KBxN mice compared to control mice that was significantly reduced by compound 001 treatment at dosage 50 mg/kg b.i.d. (Table 8).

7) Cardiotoxicity: Cell Proliferation and Viability Assay on Cardiomyocytes

Protocol Assays

WST-1 cell survival/proliferation assay (Roche Diagnostic ref No 1644807) was performed on both primary human adult cardiomyocytes and rat neonatal cardiac myocytes.

Human cardiomyocytes were isolated from normal human ventricle tissue of the adult heart and were able to proliferate for a number of passage. Neonatal ventricular Clonetics® Rat Cardiac Myocytes (P1-3) retained their contractile property and were electrophysiologically active in culture. $1.10^4$ primary rat cells or $2-2.5 \ 10^4$ adult human cells were plated per well of a 96 wells plates. The cells were allowed to adhere to the plates for 5 days before drug treatment. Treatment was initiated by addition of a 2× drug solution of ½ serial dilutions ranging from 0 to 10 µM. Cells were grown for 48 h at 37° C. and then incubated with 10 µl/well of WST-1 reagent for 4 h at 37° C. The amount of formazan dye formed was quantified by its absorbance at 450 nm using a scanning multiwell spectrophotometer (MultiSkan MS, Thermo-LabSystems, France). A blank well without cells was used as a background control for the spectrophotometer and all assays were performed in triplicate.

Experimental Results

Cardiac toxicity of drugs can be determined in vitro using primary cardiomyocytes. The cytotoxicity of tests substances was analyzed on rat and human cardiomyocytes using an in vitro proliferation and survival assay. Results are reported in Table.

TABLE 9

Drug-induced cytotoxicity of human and rat cardiomyocytes

| | Drug-induced cytotoxicity ($IC_{50}$ µM) (% cell viable at 1 µM) | |
|---|---|---|
| Drugs | Hu-CM | Rat-CM |
| Compound 001 | 10 (+14%) | 10 (−2%) |
| R406 | 2.6 (−18%) | <1 (−60%) |

Hu-CM = Human Cardiac Myocyte,
Rat-CM = Rat Cardiac Myocyte

Comments on the Experiments and Results

The above data dearly showed that compound 001 exhibited no cytotoxic effect on both human and rat cardiomyocytes at concentrations up to 10 µM. In contrast, R406 was toxic to both human and rat cardiomyocytes with an $IC_{50} \leq 2.6$ µM.

8) Cardiotoxicity: Functional hERG/Kv11.1 Potassium Chanel

Protocol Assays

The activity of the test compounds on the hERG potassium channel was evaluated using a binding assay provided by Invitrogen (Predictor hERG Fluorescence Polarization assay Kit PV5365). The test was performed at a single concentration of 3 µM of drug. E-4031, a well-known selective inhibitor of hERG potassium channel, is used as positive control. The data are expressed as a percentage of hERG inhibition, 100% corresponding to the inhibition obtained with E-4031 and 0% with the solvent DMSO (negative control).

Experimental Results

Cardiotoxicity effects may arise through undesired blockage of the human Ether-a-go-go-related (hERG) potassium channel. Therefore, evaluating the effect on hERG channel function is essential in the development of small-molecule therapy in order to predict its potential cardiotoxic side-effects. The binding assay, the "predictor hERG fluorescence polarization assay" (Invitrogen PV5365), was used to determine the activity of compound 001 on hERG function (Table 10).

TABLE 10

Drug-induced inhibition of hERG function

| Drugs | hERG % inhibition at 3 µM |
|---|---|
| Compound 001 | 0 |
| R406 | 5 |

Comments on the Experiments and Results

Compound 001 had no effect on hERG function.

9) Intracellular ROS in Cardiomyocytes

Protocol Assays $2 \times 10^3$ human cardiomyocytes (Promocell C-12810) or $4 \times 10^4$ rat neonatal cardiac myocytes (R-CM-561 Lonza) were seeded per well of a 96-well plate (black wall for fluorimetry usage (655090 Greiner Bio one)) 24 hours before drug treatment. Treatment was initiated by addition of a drug solution for a 10 µM final concentration. Doxorubicin was used at 5 µM as positive control for the induction of ROS. After 8 hours treatment with drugs, cells were loaded with 10 µM of CM-H2DCFDA (C6827 Invitrogen) for 1 hour, followed by 2 washes in PBS. CM-H2DCFDA is a membrane permeable reagent that can be enzymatically converted to dichlorodihydrofluorescein (DCF) in the presence of ROS. Fluorescent DCF was detected using a fluorescence spectrophotometer (BMG Labtech) with excitation of 485 nm and emission of 560 nm. The results were expressed as a relative percent of DCF-fluorescence in control cells.

Experimental Results

Monitoring drug-induced increase in the production of reactive oxygen species (ROS) in cardiomyocyte may be important to predict the cardiotoxic side effects of a drug (Table 11). The production of ROS in human and rat cardiomyocytes was studied following 8 hours drug treatment at concentration of 10 µM. The results were expressed as a percent relative to the production of ROS induced by the cardiotoxic chemotherapeutic agent doxorubicin (100%).

TABLE 1

Drug-induced ROS production in human and rat cardiomyocytes

| | Activity relative to doxorubicine (100%) | |
|---|---|---|
| Drugs | Hu-CM | Rat-CM |
| Compound 001 | 0 | 0 |

Hu-CM = Human Cardiac Myocyte,
Rat-CM = Rat Cardiac Myocyte

Comments on the Experiments and Results

These results demonstrated that compound 001 did not induce significant increase in cardiac production of ROS.

10) Mitochondrial Function

Protocol Assays

Drug-induced mitochondrial toxicity was evaluated by monitoring oxygen consumption using a Clark oxygen electrode on mitochondria isolated from heart of healthy mouse (Mitologics S.A.S, France). Briefly, isolated mitochondria are placed at 37° C. in a sealed chamber that is exposed to the surface of a Clark oxygen electrode. The presence of oxygen caused the electrode to deliver a current to the oxygen monitor, which amplified the current and converted it to a voltage output that was directly proportional to the concentration of oxygen in the chamber. Drug-induced mitochondrial toxicity was also evaluated by monitoring mitochondrial ATP production using a cell-based assay (Mitochondrial ToxGlo™ assay, Promega Corporation (cat#G8000)). This multiplex assay measured concurrently cell membrane integrity as a function of cytotoxicity, and mitochondrial function via ATP production, thus distinguishing between compounds that exhibited mitochondrial toxicity versus overt cytotoxicity. General toxicity was characterized by a decrease in ATP production and a loss of membrane integrity whereas mitochondrial toxicity resulted in decreased ATP production with little to no change in membrane integrity. The test was performed on HepG2 tumor cell line grown in galactose medium in order to force the cancer cells to produce ATP via oxidative phosphorylation (crabtree effect). Cells were treated for 2 hours with 20 µM drug before analysis of ATP detection (Luminescent signal) and cytotoxicity (Fluorescent signal) as described by manufacturers using PHERAstar and POLARstar OMEGA microplate readers respectively (BMG Labteck Sari).

Experimental Results

Mitochondrial dysfunction is a major mechanism of drug-induced toxicity. Oxygen consumption is one of the most informative and direct measures of mitochondrial function. In order to evaluate the potential mitochondrial toxicity of test compounds, $O_2$ consumption measurement was performed in the presence of drugs using an oxygen-sensitive probe (MitoXpress-Xtra, Luxcel Biosciences).

The oxygen consumption was analyzed during 20 min of drug treatment at concentrations of 40 and 80 µM (Table).

TABLE 2

Drug-induced inhibition of $O_2$ consumption

| Drugs | ATP production relative to DMSO (100%) Mito ToxGlo ™ | Cytotoxicity relative to DMSO (0%) Mito ToxGlo ™ |
|---|---|---|
| Compound 001 | 104% | 11% |
| R406 | 105% | 15% |

Comments on the Experiments and Results

Data showed that compound 001 did not exhibit inhibition of cardiac mitochondria ATP production (104% compare to 100% DMSO control) with low cytotoxicity (11%). These results showed that compound 001 did not affect mitochondrial function in HepG2 cells in the experimental conditions used.

11) AMES Mutagenic Assay

Protocol Assays

Mutagenic activity of test compounds and their metabolites (produced by rat liver S9 fraction) was evaluated in the *Salmonella typhimurium* strains TA100 and TA98 according to the Ames assay (Toxicology in vitro, (2001), 15: 105-114). Both strains were treated with various concentrations of test compounds ranging from 0.5 to 1000 µg and incubated overnight at 37° C. Analysis of mutagenicity was then performed against TA100 and TA98 strains in comparison to positive controls 2-Nitrofluorene (TA98) and Sodium Azide (TA100) without S9 fraction, and 2-Anthramine with rat S9 mix (TA98 and TA100). The results are expressed as a mutagenicity ratio in comparison to solvent controls. A test substance was considered as active if mutagenicity ratio is ≥2.

Experimental Results

The numbers of revertant colonies per plate in TA98 and TA100 strains treated with compound 001 are reported in Table and Table respectively. The results are expressed as a ratio of the number of colonies over the number of colonies in the negative control (DMSO). The test substance was active if mutagenicity ratio is ≥2.

TABLE 3

Revertant colony numbers per plate using TA98 strain treated with compound 001

| Compound | Dose level per well (µg) | S-9 fraction | Mean revertant colony counts | SD | Ratio treated/ solvent |
|---|---|---|---|---|---|
| DMSO | | − | 4.3 | 3.2 | |
| | 0.5 | − | 7.3 | 3.2 | 1.7 |
| | 1.4 | − | 4.3 | 1.2 | 1.0 |
| | 4.1 | − | 6.3 | 1.5 | 1.5 |
| Compound 001 | 12.3 | − | 5.3 | 0.6 | 1.2 |
| | 37 | − | 8.3 | 3.5 | 1.9 |
| | 111.1 | − | 6.3 | 1.5 | 1.5 |
| | 333.3 | − | 4.3 | 3.2 | 1.0 |
| | 1000 | − | 3.7 | 4.0 | 0.8 |
| 2-NF | 0.25 | − | 59.7 | 8.5 | 13.8 |
| DMSO | | + | 2.7 | 0.6 | |
| | 0.5 | + | 10.3 | 1.2 | 3.9 |
| | 1.4 | + | 7.3 | 2.1 | 2.8 |
| | 4.1 | + | 9.3 | 1.5 | 3.5 |
| Compound 001 | 12.3 | + | 6.7 | 4.0 | 2.5 |
| | 37 | + | 5.7 | 0.6 | 2.1 |
| | 111.1 | + | 7.3 | 3.2 | 2.8 |
| | 333.3 | + | 6.3 | 5.1 | 2.4 |
| | 1000 | + | 5.0 | 1.7 | 1.9 |
| 2-AM | 1 | + | 368.3 | 61.4 | 138.1 |

TABLE 4

Revertant colony numbers per plate using TA100 strain treated with compound 001

| Compound | Dose level per well (µg) | S-9 fraction | Mean revertant colony counts | SD | Ratio treated/ solvent |
|---|---|---|---|---|---|
| DMSO | | − | 26.3 | 6.4 | |
| | 0.5 | − | 32.0 | 4.4 | 1.2 |
| | 1.4 | − | 24.7 | 11.7 | 0.9 |
| | 4.1 | − | 23.7 | 1.5 | 0.9 |
| Compound 001 | 12.3 | − | 21.0 | 7.8 | 0.8 |
| | 37 | − | 21.0 | 3.6 | 0.8 |
| | 111.1 | − | 26.7 | 2.5 | 1.0 |
| | 333.3 | − | 23.7 | 2.3 | 0.9 |
| | 1000 | − | 32.0 | 4.6 | 1.2 |
| NAN3 | 1 | − | 206.0 | 21.3 | 7.8 |
| DMSO | | + | 25.7 | 5.0 | |
| | 0.5 | + | 26.7 | 10.7 | 1.0 |
| | 1.4 | + | 26.0 | 8.7 | 1.0 |
| | 4.1 | + | 26.7 | 5.0 | 1.0 |
| Compound 001 | 12.3 | + | 25.3 | 4.2 | 1.0 |
| | 37 | + | 20.7 | 4.2 | 0.8 |
| | 111.1 | + | 28.0 | 7.0 | 1.1 |
| | 333.3 | + | 28.0 | 3.5 | 1.1 |
| | 1000 | + | 19.0 | 13.9 | 0.7 |
| 2-AM | 1 | + | 463.3 | 129.8 | 18.1 |

− Absence of S-9,
+ Presence of S-9,
2-NF = 2-Nitrofluorene,
NAN3 = Sodium Azide,
2-AM = 2-Anthramine

Comments on the Experiments and Results

Noteworthy increases in the number of revertants were observed in the TA98 strain with S9 mix at all tested doses. The increases exceeded the threshold of 2 fold the vehicle control value but they were not dose-related. More over the number of revertants and the corresponding individual revertants colony counts observed at these dose-levels remained within the historical range for the corresponding vehicle control. Consequently, these increases were not considered biologically relevant.

Under the experimental conditions of the studies, the test compound 001 did not show any mutagenic activity with or without liver metabolic activation system (S9 mix).

12) Early Bioavailability Determination

Protocol Assays

Early screen was conducted to estimate plasma concentrations of test compounds obtained after oral or intravenous administration to Sprague Dawley rats. DMSO was used as vehicle for oral and intravenous administration. In short, 4 male Sprague Dawley rats around 5 weeks old were used. Drugs were administered PO (10 mg/kg) or IV (2 mg/kg). Blood samples were collected at defined time schedule and analysed using LC-MS/MS determination for PK parameters calculations.

Experimental Results

PK parameters were calculated based on mean data and are presented in Table.

TABLE 5

| | | | Dose (mg/kg) | Cmax (ng/mL) | Tmax (h) | $AUC_{24}$ (ng/mL*h) | $t_{1/2}$ (h) | Cl (L/h/kg) | Vd (L/kg) | $F_{24}$ (%) |
|---|---|---|---|---|---|---|---|---|---|---|
| Compound | Route | Animal | | | | | | | | |
| 001 | IV | Mean | 2 | 869 | 0.083 | 1060 | 0.6 | 0.9 | 0.9 | 97.5 |
| | PO | Mean | 10 | 122 | 3 | 1034 | 2.1 | 1 | 2.9 | |

PK parameters calculated based on mean data

Cmax (ng/mL) = maximal plasma concentration,
Tmax (h) = First time to reach Cmax,
AUCt(ng/mL*h) = area under the plasma concentration-time curve from administration up to the last quantifiable concentration at time t,
Absolute bioavailability = F(%) = (AUC PO/dose PO)/(AUC IV/dose IV)*100.

Comments on the Experiments and Results

Compound 001 had excellent pharmacokinetic properties with a bioavailability of 97.5%.

In these in vitro and in vivo studies, the inventor observed a very effective inhibition of SYK kinase activity by the class of compounds of formula (I) as presently disclosed. Using established models in toxicological and physiological test systems to evaluate in vitro cardiotoxicity, mutagenicity and biodisponibility, the inventors demonstrated that anti-SYK compounds of formula (I) had good safety prolife.

While the present invention has been described with reference to the specific examples thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and score of the present invention. All such modifications are intended to be within the scope of the claims appended hereto.

The invention claimed is:

1. A compound of formula (I) or a pharmaceutically acceptable salt thereof:

(I)

wherein
R1, R2, R3 and R4 are each independently selected from:
hydrogen,
cyano,
$CF_3$,
halogen,
an alkyl group optionally substituted with a heterocycle,
an alkoxy group optionally substituted with a heterocycle,
a solubilising group,
a heterocycle,
—CO—NRR',
—SO₂—NRR',
—NRR',
—NR—CO—R' and
—NR—SO₂R' group
wherein R and R' are each independently hydrogen or alkyl group;
W is aryl or heteroaryl group, unsubstituted or substituted by one or more substituents selected from:
cyano,
$CF_3$,
halogen,
an alkyl group optionally substituted with a heterocycle,
a cycloalkyl group,
an alkoxy group optionally substituted with a heterocycle,
an aryl group,
a heteroaryl group,
a heterocycloalkyl group,
a solubilising group,
—CO—NRR',
—SO₂—NRR',
—NRR',
—NR—CO—R' and
—NR—SO₂R' group,
wherein R and R' are each independently hydrogen or alkyl group;
X is selected from the group consisting of O, S, N(R5), N[C(=O)R6] and (CH₂)n wherein n is 0, 1 or 2, R5 and R6 are each independently hydrogen or C1-4alkyl group;
Y is (CH₂)m wherein m is 1, 2, 3 or 4;
Z is (CH₂)p wherein p is 1 or 2.

2. The compound according to claim 1 or a pharmaceutically acceptable salt thereof, wherein X is (CH₂)n, n is 0, 1 or 2 and m and p are 1.

3. The compound according to claim 1 or a pharmaceutically acceptable salt thereof, wherein W is a substituted heteroaryl.

4. The compound according to claim 3 or a pharmaceutically acceptable salt thereof, wherein the heteroaryl is a 5-8 membered monosubstituted, monocyclic ring containing at least one nitrogen atom.

5. The compound according to claim 4 or a pharmaceutically acceptable salt thereof, wherein the heteroaryl is pyrimidin-2-yl.

6. The compound according to claim 1 or a pharmaceutically acceptable salt thereof, wherein each of the one or more substituents of W is independently selected in the group consisting of:
cyano,
$CF_3$,
halogen,
an alkyl group optionally substituted with a heterocycle, a cycloalkyl group,
an alkoxy group optionally substituted with a heterocycle,
an aryl group,
a heteroaryl group and
a heterocycloalkyl group.

7. The compound according to claim 1 or a pharmaceutically acceptable salt thereof, wherein at least three of R1, R2, R3 and R4 are hydrogen.

8. The compound according to claim 1 having formula (II) or a pharmaceutically acceptable salt thereof,

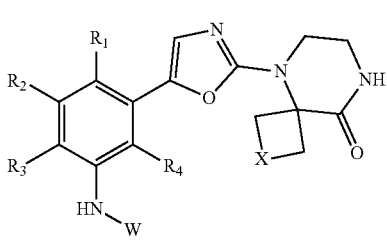

(II)

wherein R1, R2, R3, R4 and W are as defined in claim 1, X is (CH$_2$)n and n is 0, 1 or 2.

9. The compound according to claim 8 having formula (III) or a pharmaceutically acceptable salt thereof,

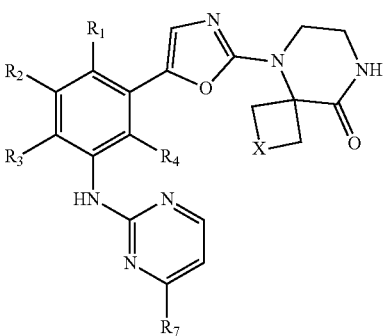

(III)

wherein R1, R2, R3, R4 and X are as defined in claim 8, and R7 is selected from the group consisting of:
hydrogen,
cyano,
CF$_3$,
halogen,
an alkyl group,
a cycloalkyl group,
an alkoxy group,
an aryl group,
a heteroaryl group,
a heterocycloalkyl group,
a solubilising group, and
—NRR' group wherein R and R' are each independently hydrogen or an alkyl group.

10. The compound according to claim 1 selected from the group consisting of:
4-{5-[3-(4-Methyl-pyrimidin-2-ylamino)-phenyl]-oxazol-2-yl}-4,7-diaza-spiro[2.5]octan-8-one;
2-{3-[2-(8-Oxo-4,7-diaza-spiro[2.5]oct-4-yl)-oxazol-5-yl]-phenylamino}-pyrimidine-4-carbonitrile;
4-{5-[3-Morpholin-4-ylmethyl-5-(4-trifluoromethyl-pyrimidin-2-ylamino)-phenyl]-oxazol-2-yl}-4,7-diaza-spiro[2.5]octan-8-one;
4-{5-[2-(2-Morpholin-4-yl-ethoxy)-5-(4-thiophen-2-yl-pyrimidin-2-ylamino)-phenyl]-oxazol-2-yl}-4,7-diaza-spiro[2.5]octan-8-one;
4-{5-[3-Methyl-5-(4-trifluoromethyl-pyrimidin-2-ylamino)-phenyl]-oxazol-2-yl}-4,7-diaza-spiro[2.5]octan-8-one;
4-{5-[3-(4-Methyl-pyrimidin-2-ylamino)-5-morpholin-4-ylmethyl-phenyl]-oxazol-2-yl}-4,7-diaza-spiro[2.5]octan-8-one;
4-{5-[3-(4-Ethyl-pyrimidin-2-ylamino)-phenyl]-oxazol-2-yl}-4,7-diaza-spiro[2.5]octan-8-one;
4-{5-[3-(4-Trifluoromethyl-pyrimidin-2-ylamino)-phenyl]-oxazol-2-yl}-4,7-diaza-spiro[2.5]octan-8-one;
6-{5-[3-(4-Methyl-pyrimidin-2-ylamino)-phenyl]-oxazol-2-yl}-6,9-diaza-spiro[4.5]decan-10-one;
4-{5-[3-(4-Phenyl-pyrimidin-2-ylamino)-phenyl]-oxazol-2-yl}-4,7-diaza-spiro[2.5]octan-8-one;
5-{5-[3-(4-Isopropyl-pyrimidin-2-ylamino)-phenyl]-oxazol-2-yl}-5,8-diaza-spiro[3.5]nonan-9-one;
5-{5-[3-(4-Methyl-pyrimidin-2-ylamino)-phenyl]-oxazol-2-yl}-5,8-diaza-spiro[3.5]nonan-9-one;
4-{5-[3-(4-Isopropyl-pyrimidin-2-ylamino)-phenyl]-oxazol-2-yl}-4,7-diaza-spiro[2.5]octan-8-one;
4-{5-[3-(4-Morpholin-4-yl-pyrimidin-2-ylamino)-phenyl]-oxazol-2-yl}-4,7-diaza-spiro[2.5]octan-8-one;
4-{5-[3-(4-Thiophen-2-yl-pyrimidin-2-ylamino)-phenyl]-oxazol-2-yl}-4,7-diaza-spiro[2.5]octan-8-one;
5-{5-[3-(4-Trifluoromethyl-pyrimidin-2-ylamino)-phenyl]-oxazol-2-yl}-5,8-diaza-spiro[3.5]nonan-9-one;
4-{5-[2-(2-Morpholin-4-yl-ethoxy)-5-(4-trifluoromethyl-pyrimidin-2-ylamino)-phenyl]-oxazol-2-yl}-4,7-diaza-spiro[2.5]octan-8-one;
4-{5-[2-Fluoro-5-(4-methyl-pyrimidin-2-ylamino)-phenyl]-oxazol-2-yl}-4,7-diaza-spiro[2.5]octan-8-one;
4-{5-[3-(4-Pyridin-3-yl-pyrimidin-2-ylamino)-phenyl]-oxazol-2-yl}-4,7-diaza-spiro[2.5]octan-8-one;
4-{5-[2-Methyl-3-(4-methyl-pyrimidin-2-ylamino)-phenyl]-oxazol-2-yl}-4,7-diaza-spiro[2.5]octan-8-one;
4-{5-[3-(4-Methyl-pyridin-2-ylamino)-phenyl]-oxazol-2-yl}-4,7-diaza-spiro[2.5]octan-8-one;
4-{5-[3-(Thiazol-2-ylamino)-phenyl]-oxazol-2-yl}-4,7-diaza-spiro[2.5]octan-8-one;
and a pharmaceutically acceptable salt thereof.

11. The compound according to claim 10 which is 4-{5-[3-(4-Methyl-pyrimidin-2-ylamino)-phenyl]-oxazol-2-yl}-4,7-diaza-spiro[2.5]octan-8-one or a pharmaceutically acceptable salt thereof.

12. A pharmaceutical composition comprising a compound according to claim 1, or a pharmaceutically acceptable salt thereof and one or more pharmaceutically acceptable excipients and/or carriers.

13. The pharmaceutical composition according to claim 12, comprising the compound as defined in claim 1, or a pharmaceutically acceptable salt thereof as sole active pharmaceutical ingredient or in combination with another active pharmaceutical ingredient.

14. A process for the manufacture of a compound as defined in claim 1, or a pharmaceutically acceptable salt thereof, said process comprising a step of reacting a compound of formula (i)

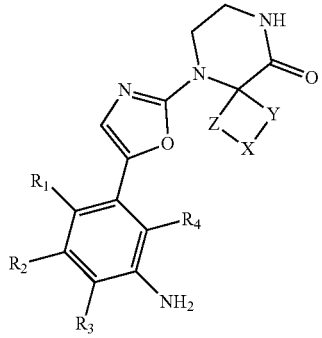
(i)

with a compound of formula W-G,
wherein R1 to R4, W, X, Y and Z are as defined in claim 1, and G is halogen.

15. A process for the manufacture of a compound as defined in claim 1, or a pharmaceutically acceptable salt thereof, said process comprising a step of reacting a compound of formula (ii)

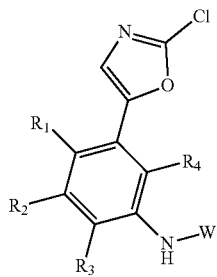
(ii)

with a compound of formula (iii)

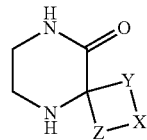
(iii)

wherein R1 to R4, W, X, Y and Z are as defined in claim 1.

16. A compound according to claim 1, or a pharmaceutically acceptable salt thereof, for use as a medicament.

17. A compound according to claim 1, or a pharmaceutically acceptable salt thereof, for use in treating a disease or disorder associated with unregulated or deregulated tyrosine kinase activity, wherein the disease or disorder is selected from the group consisting of hematological disorders, proliferative disorders, autoimmune disorders, metabolic disorders, inflammatory diseases, allergic diseases and neurological diseases.

18. A compound according to claim 1, or a pharmaceutically acceptable salt thereof, for use in treating a disease or disorder associated with signal transduction mediated by SYK, wherein the disease or disorder is selected from the group consisting of hematological disorders, proliferative disorders, autoimmune disorders, metabolic disorders, inflammatory diseases, allergic diseases and neurological diseases.

19. The pharmaceutical composition according to claim 13, comprising a compound defined in claim 1, or a pharmaceutically acceptable salt thereof, and another active pharmaceutical ingredient as a combined preparation for sequential, simultaneous or separate use in the treatment of a disease or disorder selected from the group consisting of hematological disorders, proliferative disorders, autoimmune disorders, metabolic disorders, inflammatory diseases, allergic diseases and neurological diseases.

* * * * *